United States Patent
Han et al.

(10) Patent No.: US 11,467,149 B2
(45) Date of Patent: Oct. 11, 2022

(54) ELECTRONIC APPARATUS AND CONTROLLING METHOD THEREOF

(71) Applicant: SAMSUNG ELECTRONICS CO., LTD., Suwon-si (KR)

(72) Inventors: Jeongsu Han, Suwon-si (KR); Taegyoon Noh, Suwon-si (KR); Gwangjin Jung, Suwon-si (KR); Junhoe Choi, Suwon-si (KR); Jongsoo Hong, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 415 days.

(21) Appl. No.: 16/709,058

(22) Filed: Dec. 10, 2019

(65) Prior Publication Data

US 2020/0182848 A1 Jun. 11, 2020

(30) Foreign Application Priority Data

Dec. 10, 2018 (KR) .................. 10-2018-0158246

(51) Int. Cl.
*G01N 33/02* (2006.01)
*G06T 7/90* (2017.01)
(Continued)

(52) U.S. Cl.
CPC ............. *G01N 33/02* (2013.01); *G01N 21/01* (2013.01); *G01N 21/84* (2013.01); *G06T 7/90* (2017.01);
(Continued)

(58) Field of Classification Search
CPC .. G01N 2021/8466; G06T 2207/30128; G06T 7/90; H05B 45/20; H01L 25/167;
(Continued)

(56) References Cited

U.S. PATENT DOCUMENTS 3,910,701 A * 10/1975 Henderson ........... G01N 21/474
356/73
4,851,914 A * 7/1989 Pfanhouser .......... H04N 5/2353
348/E5.037
(Continued)

FOREIGN PATENT DOCUMENTS

EP 0375881 7/1990
EP 8-266424 10/1996
(Continued)

OTHER PUBLICATIONS

International Search Report dated Apr. 9, 2020 in International Patent Application No. PCT/KR2019/017379.
(Continued)

*Primary Examiner* — Georgia Y Epps
*Assistant Examiner* — Don J Williams
(74) *Attorney, Agent, or Firm* — Staas & Halsey LLP

(57) ABSTRACT

Disclosed herein is an electronic apparatus and method capable of identifying a state of an object. The electronic apparatus includes a light-emitting diode array configured to transmit light beams having different wavelengths, a photodiode array configured to receive the light beams, a display, and a processor configured to control the light-emitting diode array to transmit the light beams having the different wavelengths toward an object, identify a state of the object based on intensities reflected on the object according to the light beams having the different wavelengths that are received by the photodiode array, and display information about the state of the object on the display.

18 Claims, 23 Drawing Sheets

(51) Int. Cl.
  *H05B 45/20* (2020.01)
  *G01N 21/01* (2006.01)
  *G01N 21/84* (2006.01)
  *H01L 25/075* (2006.01)
  *H01L 25/16* (2006.01)
  *H01L 27/146* (2006.01)
  *H01L 33/50* (2010.01)
  *H04N 5/232* (2006.01)

(52) U.S. Cl.
  CPC ........ *H01L 25/0753* (2013.01); *H01L 25/167* (2013.01); *H01L 27/14643* (2013.01); *H01L 33/50* (2013.01); *H04N 5/23229* (2013.01); *H05B 45/20* (2020.01); *G01N 2021/0181* (2013.01); *G01N 2021/8466* (2013.01); *G06T 2207/30128* (2013.01)

(58) Field of Classification Search
  CPC ............... H01L 27/14643; H01L 33/50; H01L 25/0753
  See application file for complete search history.

(56) References Cited

U.S. PATENT DOCUMENTS

| | | |
|---|---|---|
| 2008/0138841 A1 | 6/2008 | Vegvary et al. |
| 2009/0147260 A1 | 6/2009 | Costa et al. |
| 2018/0017251 A1 | 6/2018 | Rosen et al. |

FOREIGN PATENT DOCUMENTS

| | | |
|---|---|---|
| JP | 8-266424 | 10/1996 |
| JP | 2007-147316 | 6/2007 |
| JP | 4162345 | 10/2008 |
| JP | 5294757 | 9/2013 |
| JP | 2017-223420 | 12/2017 |
| KR | 10-0676279 | 2/2007 |
| KR | 10-2017-0128657 | 11/2017 |
| KR | 10-2018-0036150 | 4/2018 |

OTHER PUBLICATIONS

Partial European Search Report dated May 19, 2020 in European Patent Application No. 19215035.7.

* cited by examiner

ELECTRONIC APPARATUS AND CONTROLLING METHOD THEREOF

CROSS-REFERENCE TO RELATED APPLICATION

This application claims the benefit of Korean Patent Application No. 10-2018-0158246, filed on Dec. 10, 2018 in the Korean Intellectual Property Office, the disclosure of which is incorporated herein by reference.

BACKGROUND

1. Field

Embodiments of the present disclosure relate to an electronic apparatus and a controlling method thereof, and more particularly, to an electronic apparatus capable of identifying a state of an object, and a controlling method thereof.

2. Description of the Related Art

Electronic apparatuses may include optical sensors capable of transmitting light, receiving light reflected from an object, and analyzing the received light to identify the object, calculate a distance to the object, or identify a state of the object.

Typical optical sensors transmit monochromatic light (light with maximum intensity at a single wavelength) and receive monochromatic light reflected from an object. However, the optical sensors using the monochromatic light can acquire only limited information about the object. For example, it is difficult for the optical sensors using the monochromatic light to detect a color of the object.

Alternatively, cameras are also used to analyze an object. The camera may receive red light, green light, and blue light and may detect the shape and color of the object through a combination of red light, green light, and blue light. However, the camera can also acquire only information due to red light, green light, and blue light.

SUMMARY

In accordance with one aspect of the present disclosure, an electronic apparatus includes a light-emitting diode array capable of transmitting light beams having different wavelengths, a photodiode array capable of receiving the light beams, a display, and a processor configured to control the light-emitting diode array to transmit the light beams having the different wavelengths toward an object, identify a state of the object based on intensities of the received light beams having the different wavelengths received by the photodiode array, and display information about the state of the object on the display.

In accordance with one aspect of the present disclosure, a controlling method of an electronic apparatus includes transmitting, by a light-emitting diode array, light beams having different wavelengths toward an object, receiving, by a photodiode array, the light beams having the different wavelengths reflected on the object, identifying a state of the object based on intensities of the received light beams having the different wavelengths, and displaying information about the state of the object on a display.

In accordance with one aspect of the present disclosure, an electronic apparatus includes a chamber capable of accommodating a food, a plurality of light-emitting diodes capable of transmitting light beams having different wavelengths, a plurality of photodiodes capable of receiving the light beams, a display, and a processor configured to control the plurality of light-emitting diodes to sequentially transmit the light beams having the different wavelengths toward the food provided in the chamber and display a state of the food on the display based on intensities of the light beams having the different wavelengths received by the photodiodes.

Additional aspects of the disclosure will be set forth in part in the description which follows and, in part, will be obvious from the description, or may be learned by practice of the disclosure.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
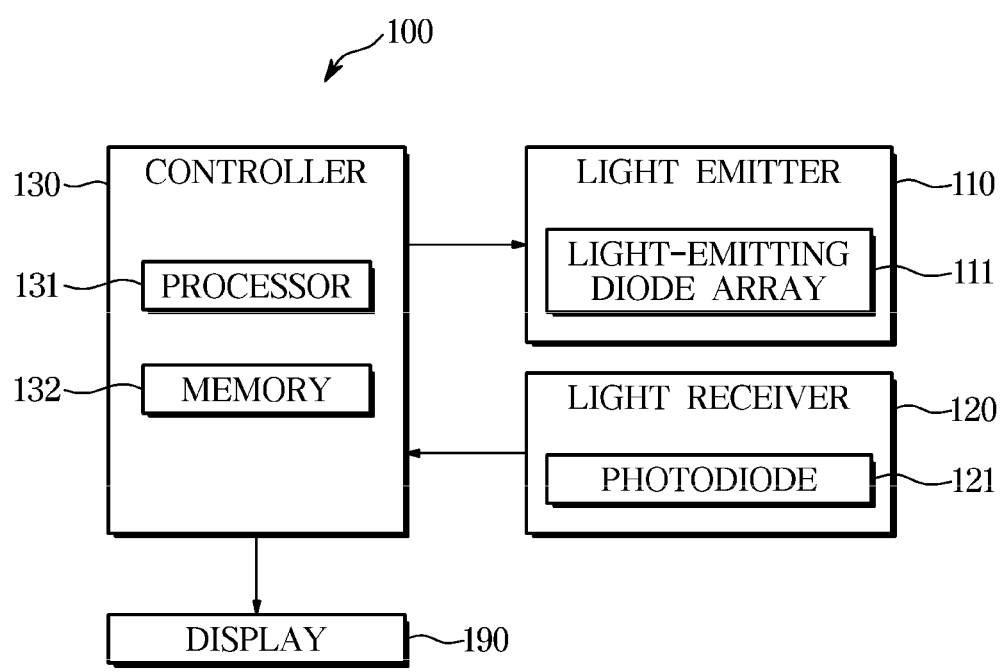
FIG. 1 is a view illustrating a configuration of an electronic apparatus according to one embodiment.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed as is known in the art, with the exception of operations necessarily occurring in a particular order. In addition, respective descriptions of well-known functions and constructions may be omitted for increased clarity and conciseness.

Additionally, exemplary embodiments will now be described more fully hereinafter with reference to the accompanying drawings. The exemplary embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. Like numerals denote like elements throughout.

It will be understood that, although the terms first, second, etc. may be used herein to describe various elements, these elements should not be limited by these terms. These terms are only used to distinguish one element from another. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present.

The terminology used herein is for the purpose of describing particular embodiments only and is not intended to be limiting. As used herein, the singular forms "a," "an," and "the," are intended to include the plural forms as well, unless the context clearly indicates otherwise.

Reference will now be made in detail to the exemplary embodiments of the present disclosure, examples of which are illustrated in the accompanying drawings, wherein like reference numerals refer to like elements throughout.

The expression, "at least one of a, b, and c," should be understood as including only a, only b, only c, both a and b, both a and c, both b and c, or all of a, b, and c.

Hereinafter, a principle of action and embodiments of the present disclosure will be described with reference to the accompanying drawings.

It is an aspect of the present disclosure to provide an electronic apparatus using a plurality of light beams having different wavelengths.

It is an aspect of the present disclosure to provide an electronic apparatus capable of identifying a state of an object using a plurality of light beams having different wavelengths.

It is an aspect of the present disclosure to provide an electronic apparatus capable of identifying cooking information of a food using a plurality of light beams having different wavelengths.

It is an aspect of the present disclosure to provide an electronic apparatus capable of identifying whether a food is rotten using a plurality of light beams having different wavelengths.

Figure 2:
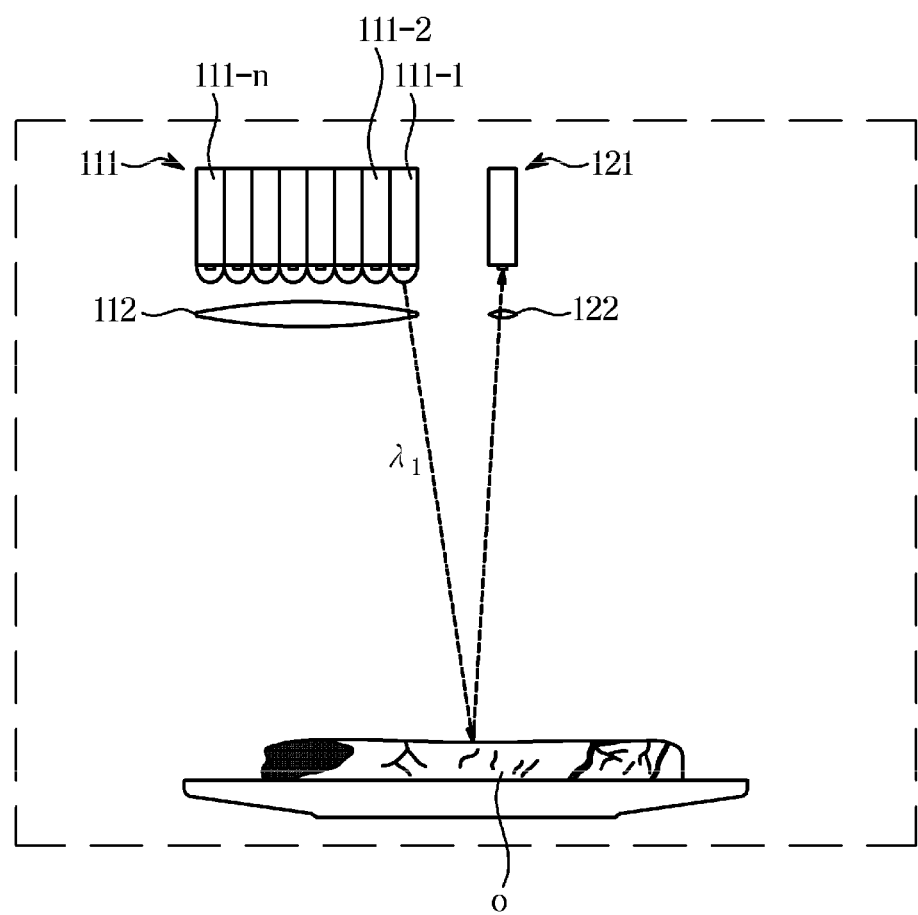
FIGS. 2 and 3 are views illustrating examples of the electronic apparatus according to one embodiment.
Figure 3:
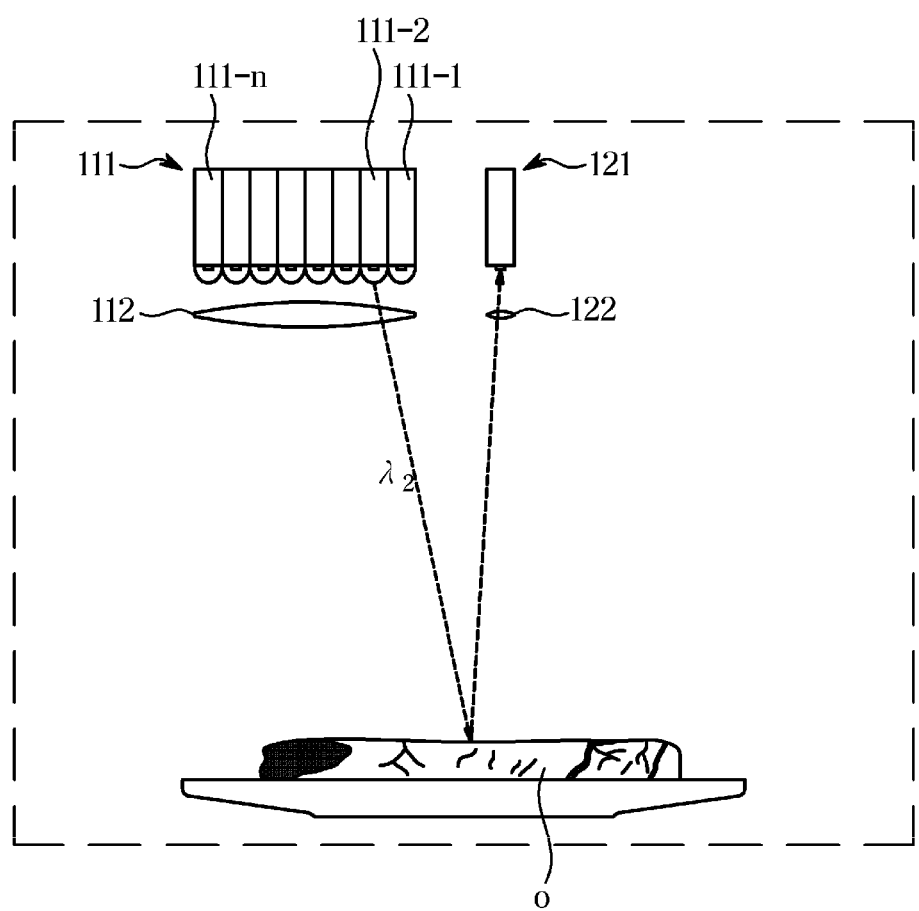
Figure 4:
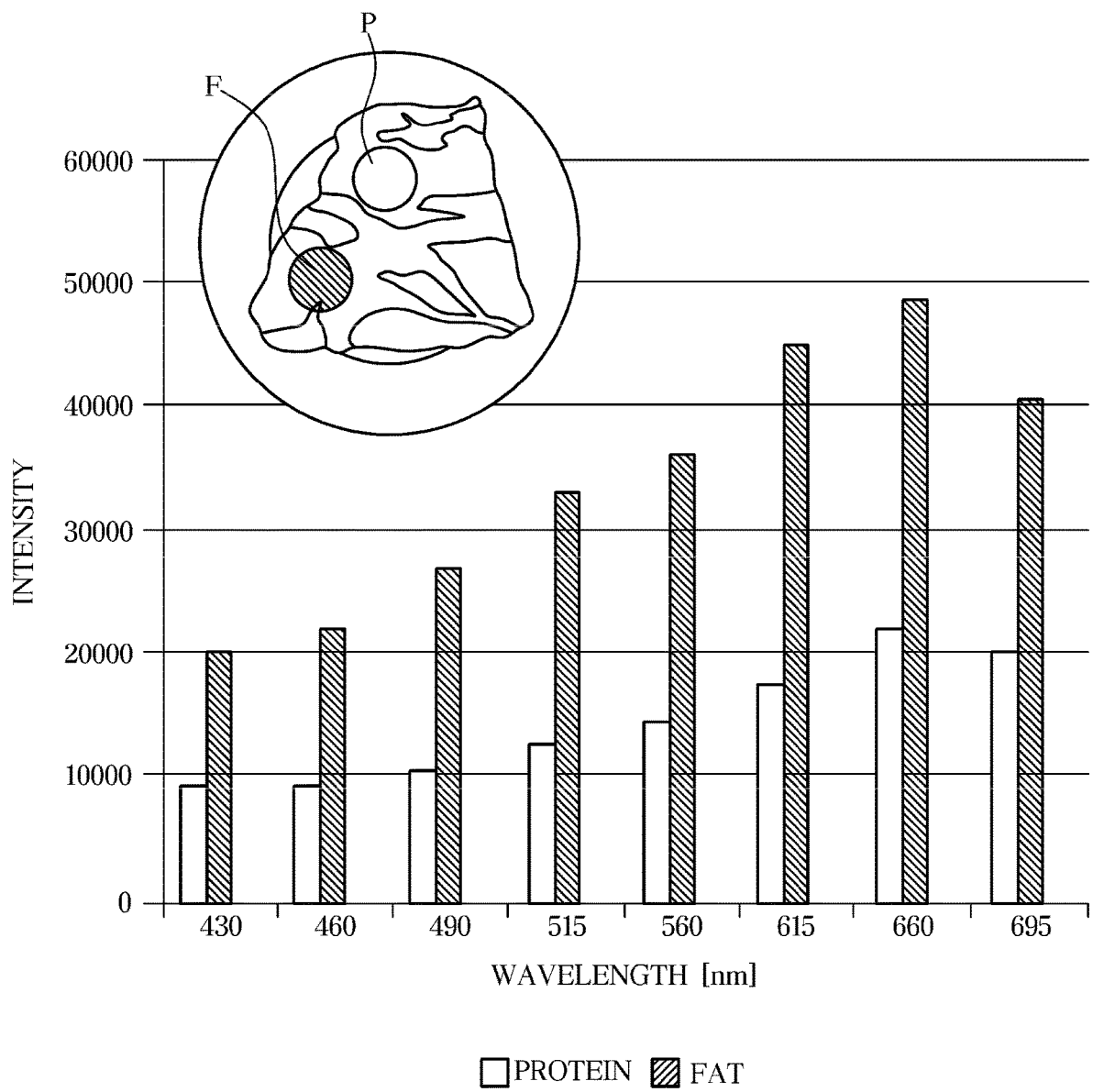
FIG. 4 is a graph showing reception intensities of light beams having different wavelengths.
Figure 5:
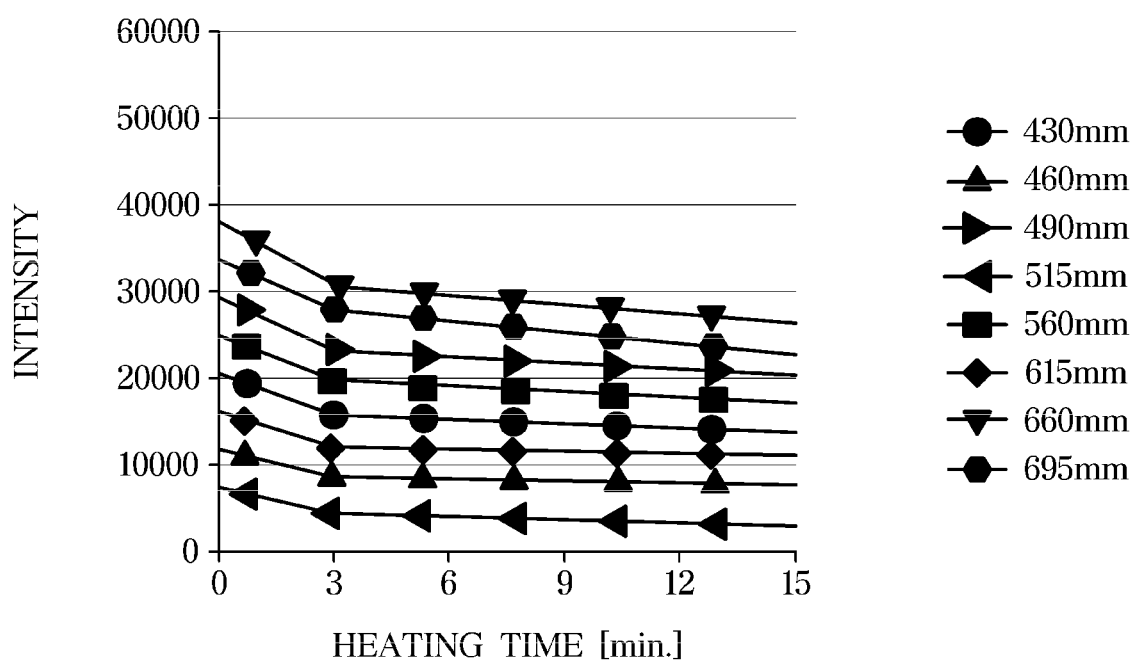
FIGS. 5 and 6 are graphs showing changes in reception intensities of light beams having different wavelengths.
Figure 6:
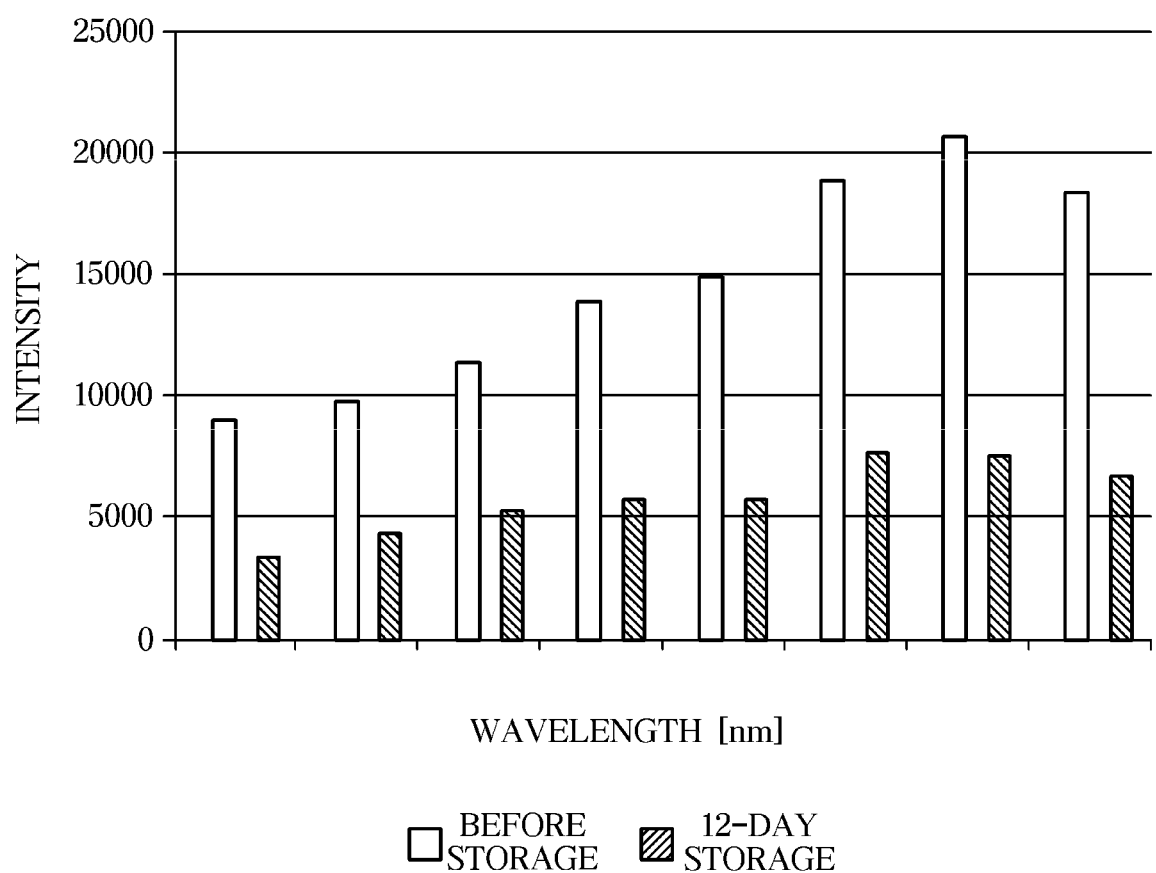

FIG. 1 is a view illustrating a configuration of an electronic apparatus according to one embodiment. FIGS. 2 and 3 are views illustrating examples of the electronic apparatus according to one embodiment. FIG. 4 is a graph showing reception intensities of light beams having different wavelengths. FIGS. 5 and 6 are graphs showing changes in reception intensities of light beams having different wavelengths.

Referring to FIGS. 1, 2, 3, 4, 5, and 6, an electronic apparatus 100 includes a light emitter 110 capable of transmitting a plurality of light beams having maximum intensities at different wavelengths (hereinafter, referred to as "plurality of light beams having different wavelengths") toward an object, a light receiver 120 capable of receiving light beams, a controller 130 configured to control the light emitter 110, process a signal output from the light receiver 120, and identify a state of the object, and a display 190 configured to display information about the state of the object.

The light emitter 110 includes a light-emitting diode array 111 capable of transmitting a plurality of light beams having different wavelengths.

As shown in FIGS. 2 and 3, the light-emitting diode array 111 includes a first light-emitting diode 111-1, a second light-emitting diode 111-2, . . . and an $n^{th}$ light-emitting diode 111-$n$. Hereinafter, although it will be described that the light emitter 110 includes a plurality of light-emitting diodes 111-1, 111-2, . . . and 111-$n$, the present disclosure is not limited thereto. For example, the light emitter 110 may include a plurality of laser elements capable of transmitting light beams having different wavelengths. In another example, the light emitter 110 may include a light-emitting diode capable of transmitting a blue light beam or an ultraviolet light beam and a plurality of fluorescent substances capable of transmitting light beams having different wavelengths. As described above, the light emitter 110 may include various means capable of transmitting a plurality of light beams having different wavelengths.

The first light-emitting diode 111-1, the second light-emitting diode 111-2, . . . the $n^{th}$ light-emitting diode 111-$n$ may be disposed in a line. However, the present disclosure is not limited thereto. The plurality of light-emitting diodes 111-1, 111-2, . . . and 111-$n$ may be variously disposed. For example, the plurality of light-emitting diodes 111-1, 111-2, . . . and 111-$n$ may be disposed in columns and rows.

The first light-emitting diode 111-1, the second light-emitting diode 111-2, . . . and the $n^{th}$ light-emitting diode 111-$n$ may transmit light beams having different wavelengths. For example, the first light-emitting diode 111-1 may transmit a light beam having a maximum intensity at a first wavelength $\lambda_1$ (hereinafter, referred to as "light beam having a first wavelength"), and the second light-emitting diode 111-2 may transmit a light beam having a second wavelength $\lambda_2$. In addition, the $n^{th}$ light-emitting diode 111-$n$ may transmit a light beam having an $n^{th}$ wavelength $\lambda_n$.

The light beams transmitted from the plurality of light-emitting diodes 111-1, 111-2, . . . and 111-$n$ may include various light beams such as an ultraviolet light beam, a blue light beam, a green light beam, a red light beam, and an infrared light beam according to lengths of wavelengths. For example, the light-emitting diode array 111 may include four or more light-emitting diodes capable of transmitting a blue light beam, a green light beam, a red light beam, and an infrared light beam. However, the present disclosure is not limited thereto. The light-emitting diode array 111 may include five or more light-emitting diodes capable of transmitting five or more light beams having different wavelengths.

One of the first light-emitting diode 111-1, the second light-emitting diode 111-2, . . . and the $n^{th}$ light-emitting diode 111-$n$ may transmit a light beam in response to an emission control signal of the controller 130. For example, the first light-emitting diode 111-1, the second light-emitting diode 111-2, . . . and the $n^{th}$ light-emitting diode 111-$n$ may sequentially transmit light beams in response to the emission control signal of the controller 130. The first light-emitting diode 111-1 may transmit the light beam having the first wavelength $\lambda_1$, and then the second light-emitting diode 111-2 may transmit the light beam having the second wavelength $\lambda_2$. Finally, the $n^{th}$ light-emitting diode 111-$n$ may transmit the light beam having the $n^{th}$ wavelength $\lambda_n$.

As described above, the light-emitting diode array 111 may sequentially transmit the light beam having the first wavelength $\lambda_1$, the light beam having the second wavelength $\lambda_2$, . . . and the light beam having the $n^{th}$ wavelength $\lambda_n$ in response to the emission control signal of the controller 130.

A first optical member 112 configured to guide a light beam transmitted from the light-emitting diode array 111 to an object O may be provided at a side through which a light beam is transmitted from the light-emitting diode array 111.

The first optical member 112 may include, for example, an optical lens, a slit, an aperture, and the like. As described above, the first optical member 112 may include various optical means such as optical means configured to guide a light beam toward the object or optical means configured to block a light beam that is not directed toward the object.

The light beam transmitted from each of the plurality of light-emitting diodes 111-1, 111-2, . . . and 111-$n$ may be guided toward the object O by the first optical member 112.

The light beam guided toward the object O may be reflected on a surface of the object O. For example, the light beam may be irregularly reflected in various directions on the surface of the object O.

The light-emitting diode array 111 may sequentially transmit a plurality of light beams having different wavelengths, and the plurality of light beams having the different wavelengths may be reflected on the surface of the object O.

Intensity of a light beam reflected on the surface of the object O may be changed according to characteristics of the surface of the object O and a wavelength of the light beam. When intensity of the light beam having the first wavelength $\lambda_1$ and reflected on the surface of the object O is the greatest among light beams having different wavelengths, the object O may be viewed in color exhibited by the first wavelength $\lambda_1$. When intensity of a light beam having a wavelength of 580 nanometers (nm) and reflected on the surface of the object O is the greatest among light beams having different wavelengths, the object O may be viewed in yellow.

The light receiver 120 includes a photodiode 121 capable of receiving a light beam. The photodiode 121 may measure intensity of the received light beam and may transmit an electrical signal (for example, a current or voltage) (hereinafter referred to as "reception intensity signal") corresponding to the intensity of the light beam to the controller 130.

The photodiode 121 may receive light beams having various wavelengths and may measure intensities of the received light beams. For example, the photodiode 121 may receive the light beam having the first wavelength $\lambda_1$, the light beam having the second wavelength $\lambda_2$, . . . and the light beam having the $n^{th}$ wavelength $\lambda_n$ and may output reception intensity signals corresponding to intensities of the received light beams.

The photodiode 121 may receive a light beam that is transmitted from the light-emitting diode array 111 and is reflected on the object O and may measure intensity of the received light beam. For example, when the light-emitting diode array 111 transmits the light beam having the first wavelength $\lambda_1$, the photodiode 121 may measure intensity of the light beam having the first wavelength $\lambda_1$ and reflected on the object O. When the light-emitting diode array 111 transmits the light beam having the second wavelength $\lambda_2$, the photodiode 121 may measure intensity of the light beam having the second wavelength $\lambda_2$ and reflected on the object O. In addition, when the light-emitting diode array 111 transmits the light beam having the $n^{th}$ wavelength $\lambda_n$, the photodiode 121 may measure intensity of the light beam having the $n^{th}$ wavelength $\lambda_n$ and reflected on the object O.

A second optical member 122 configured to guide a light beam to the photodiode 121 may be provided at a side through which a light beam is received by the photodiode 121. The second optical member 122 may guide a light beam reflected from the object O toward the photodiode 121.

The second optical member 122 may include, for example, an optical lens, a slit, an aperture, and the like. As described above, the second optical member 122 may include various optical means such as optical means configured to guide a light beam toward the photodiode 121 or optical means configured to block a light beam that is not directed toward the photodiode 121.

The controller 130 may be electrically connected to the light emitter 110 and the light receiver 120. For example, the controller 130 may output an emission control signal to the light-emitting diode array 111 of the light emitter 110 and may receive a reception intensity signal from the photodiode 121 of the light receiver 120.

The controller 130 includes a processor 131 configured to generate the emission control signal and process the reception intensity signal and a memory 132 configured to store and/or retain a program and data for generating the emission control signal and processing the reception intensity signal.

The processor 131 may generate an emission control signal for controlling operation of the light-emitting diode array 111 based on the program and data stored and/or retained in the memory 132. For example, as shown in FIG. 2, the processor 131 may generate a first emission control signal for turning on the first light-emitting diode 111-1 configured to transmit the light beam having the first wavelength $\lambda_1$. As shown in FIG. 3, the processor 131 may generate a second emission control signal for turning on the second light-emitting diode 111-2 configured to transmit the light beam having the second wavelength $\lambda_2$. In addition, the processor 131 may generate an $n^{th}$ emission control signal for turning on the $n^{th}$ light-emitting diode 111-$n$ configured to transmit the light beam having the $n^{th}$ wavelength $\lambda_n$.

The processor 131 may process the reception intensity signal received from the photodiode 121 based on the program and data stored and/or retained in the memory 132.

The processor 131 may process a reception intensity signal in relation to an emission control signal. For example, the processor 131 may output the first emission control signal to the light-emitting diode array 111 and may store a first reception intensity received from the photodiode 121 in the memory 132 in relation to the first wavelength $\lambda_1$. The processor 131 may output the second emission control signal to the light-emitting diode array 111 and may store a second reception intensity received from the photodiode 121 in the memory 132 in relation to the second wavelength $\lambda_2$. In addition, the processor 131 may output the $n^{th}$ emission control signal to the light-emitting diode array 111 and may store an $n^{th}$ reception intensity received from the photodiode 121 in the memory 132 in relation to the $n^{th}$ wavelength $\lambda_n$.

The processor 131 may include an operational circuit, a memory circuit, and a control circuit. The processor 131 may include one chip or may include a plurality of chips. In addition, the processor 131 may include one core or may include a plurality of cores.

The memory 132 may store and/or retain the program and data for generating the emission control signal and processing the reception intensity signal.

The memory 132 may store the first reception intensity in relation to the first wavelength $\lambda_1$, the second reception intensity in relation to the second wavelength $\lambda_2$, . . . and the $n^{th}$ reception intensity in relation to the $n^{th}$ wavelength $\lambda_n$.

The memory 132 may include volatile memories such as a static random access memory (S-RAM) and a dynamic random access memory (D-RAM) and nonvolatile memories such as a read only memory (ROM), an erasable programmable read only memory (EPROM), and an electrically erasable programmable read only memory (EEPROM).

The memory 132 may include one memory element or may include a plurality of memory elements.

As described above, the controller 130 controls the light-emitting diode array 111 to sequentially transmit light beams having different wavelengths toward the object O and may store a signal indicating intensity of a light beam received by the photodiode 121.

For example, the controller 130 may control the light-emitting diode array 111 to sequentially transmit light beams having different wavelengths toward a protein portion P of a meat M. The controller 130 may control the light-emitting diode array 111 to sequentially transmit a light beam having a wavelength of 430 nm, a light beam having a wavelength of 460 nm, a light beam having a wavelength of 490 nm, a light beam having a wavelength of 515 nm, a light beam having a wavelength of 560 nm, a light beam having a wavelength of 615 nm, a light beam having a wavelength of 660 nm, and a light beam having a wavelength of 695 nm.

The controller 130 may store intensity of a light beam received by the photodiode 121 according to a light beam transmitted from the light-emitting diode array 111. The controller 130 may control the light-emitting diode array 111 to transmit the light beam having the wavelength of 430 nm and may store intensity of a light beam received by the photodiode 121 in relation to the wavelength of 430 nm. The controller 130 may control the light-emitting diode array 111 to transmit the light beams having the wavelengths from 460 nm to 695 nm and may store intensities of light beams received by the photodiode 121 in relation to the wavelengths from 460 nm to 695 nm.

As shown in FIG. 4, the controller 130 may store intensities of light beams reflected from the protein portion P of the meat M in relation to wavelengths of light beams transmitted by the light-emitting diode array 111.

The controller 130 may control the light-emitting diode array 111 to sequentially transmit light beams having different wavelengths toward a fat portion F of the meat M. In addition, the controller 130 may store intensity of a light beam received by the photodiode 121 according to a light beam transmitted from the light-emitting diode array 111.

As shown in FIG. 4, the controller 130 may store intensities of light beams reflected from the fat portion F of the meat M in relation to wavelengths of light beams transmitted by the light-emitting diode array 111.

In addition, the controller 130 may calculate a reflectance of a light beam based on a ratio of the intensity of the light beam transmitted from the light-emitting diode array 111 to the intensity of the light beam received by the photodiode 121.

The controller 130 may identify the object O based on reflection intensities (or reflectances) of light beams having different wavelengths.

As shown in FIG. 4, reflection intensities (or reflectances) of light beams having different wavelengths in the fat portion F of the meat M are different from reflection intensities (or reflectances) of the light beams having the different wavelengths in the protein portion P of the meat M. Therefore, the fat portion F of the meat M may be identified from the protein portion P of the meat M based on the reflection intensities (or reflectances) of the light beams having the different wavelengths.

In such a manner, the controller 130 may identify the object O based on reflection intensities (or reflectances) of light beams having different wavelengths. For example, the controller 130 may store reflection intensity (or reflectance) of a light beam of various objects (for example, various foods) in the form of a database with respect to each of different wavelengths. The controller 130 may compare reflection intensity (or reflectance) of a light beam by the object O to be measured, with respect to each of different wavelengths with reflection intensity (or reflectance) of a light beam with respect to each of the different wavelengths in the database. The controller 130 may identify the object O based on a comparison result.

The controller 130 may identify a degree of rottenness of a food or a degree of cooking of the food based on reflection intensities (or reflectances) of light beams having different wavelengths.

For example, a degree of rottenness of a food may be identified using a statistical regression analysis. A model indicating a degree of rottenness and/or cooking of a food may be generated using the statistical regression analysis. A model represented by Expression 1 may be used.

$$y = a_0 + a_1 * x_1 + a_2 * x_2 + \ldots + a_n * x_n \tag{1}$$

Here, y may refer to a variable indicating a degree of rottenness and/or cooking of a food, $x_1, x_2, \ldots$ and $x_n$ may respectively refer to reflection intensity of the light beam having the first wavelength $\lambda_1$, reflection intensity of the light beam having the second wavelength $\lambda_2$, . . . and reflection intensity of the light beam having the $n^{th}$ wavelength $\lambda_n$, and $a_0, a_1, a_2, \ldots$ and $a_n$ may each refer to a constant.

y may be a variable indicating a degree of rottenness of a food. For example, y may refer to a predefined value indicating a degree of rottenness of a food (hereinafter, referred to as "rottenness value"). For example, the rottenness value may be defined based on the number of microorganisms and the like.

$a_0, a_1, a_2, \ldots$ and $a_n$ may be empirically or experimentally defined. For example, a designer may irradiate light beams having different wavelengths onto a food (for example, a meat, fish, and the like) in advance and may obtain reflection intensities $x_1, x_2, \ldots$ and $x_n$ of the light beams having the different wavelengths and a rottenness value of the food. By using machine learning, a statistical analysis, or the like, the designer may calculate $a_0, a_1, a_2, \ldots$ and $a_n$ from the reflection intensities $x_1, x_2, \ldots$ and $x_n$ and the rottenness value of the food.

The controller 130 may calculate the rottenness value y of the food by respectively inputting measured reflection intensity of the light beam having the first wavelength $\lambda_1$, measured reflection intensity of the light beam having the second wavelength $\lambda_2, \ldots$ and measured reflection intensity of the light beam having the $n^{th}$ wavelength $\lambda_n$ in $x_1, x_2, \ldots$ and $x_n$ of Expression 1. In addition, the controller 130 may identify whether the food is rotten based on the rottenness value y of the food.

The degree of cooking of the food may be obtained in a similar manner. The degree of cooking of the food may be identified using a statistical regression analysis. For example, the model represented by Expression 1 may be used.

y may be a variable indicating a degree of cooking of a food. For example, y may refer to a predefined value indicating a degree of cooking of a food (hereinafter, referred to as "cooking value"). For example, the cooking value may be a value in which a degree of doneness of the food is quantified.

The controller 130 may calculate the cooking value y of the food by respectively inputting measured reflection intensity of the light beam having the first wavelength $\lambda_1$, measured reflection intensity of the light beam having the second wavelength $\lambda_2, \ldots$ and measured reflection intensity of the light beam having the $n^{th}$ wavelength $\lambda_n$ in $x_1, x_2, \ldots$ and $x_n$ of Expression 1. In addition, the controller 130 may identify whether the cooking of the food is completed based on the cooking value y of the food.

The controller 130 may measure reflection intensities (or reflectances) of light beams having different wavelengths at different times.

The controller 130 may identify a degree of rottenness of a food or a degree of cooking of the food based on changes in reflection intensities (or reflectances) of light beams having different wavelengths according to a time. In general, it is known that the entirety of a food is darkened as the food is rotten or the food is cooked.

When a food is heated, reflection intensity (or reflectance) of a light beam may be reduced according to a heating time. As shown in FIG. 5, reflection intensities of all light beams having wavelengths from 430 nm to 695 nm may be reduced according to a heating time. From this, during heating of a food, when reflection intensity (or reflectance) of the light beam having the first wavelength $\lambda_1$ is less than or equal to a first reference intensity, reflection intensity (or reflectance) of the light beam having the second wavelength $\lambda_2$ is less than or equal to a second reference intensity, . . . and reflection intensity (or reflectance) of the light beam having the $n^{th}$ wavelength $\lambda_n$ is less than or equal to an $n^{th}$ reference intensity, the controller 130 may determine that the cooking of the food has been completed.

In addition, when a food is heated, a change rate of reflection intensity (or reflectance) of a light beam may be reduced according to a heating time. As shown in FIG. 5, change sizes of the reflection intensities of all the light beams having the wavelengths from 430 nm to 695 nm are reduced according to a heating time and are saturated to constant values. From this, during heating of the food, when a change rate of the reflection intensity (or reflectance) of the light beam having the first wavelength $\lambda_1$ is less than or equal to a first reference change rate, a change rate of the reflection intensity (or reflectance) of the light beam having the second wavelength $\lambda_2$ is less than or equal to a second reference change rate, . . . and a change rate of the reflection intensity (or reflectance) of the light beam having the $n^{th}$ wavelength $\lambda_n$ is less than or equal to an $n^{th}$ reference change rate, the controller 130 may determine that the cooking of the food has been completed.

When a food is rotten, reflection intensity (or reflectance) of a light beam may be reduced according to a storage time. As shown in FIG. 6, the reflection intensities of all the light beams having the wavelengths from 430 nm to 695 nm may be reduced according to a storage time. From this, during storing of the food, when the reflection intensity (or reflectance) of the light beam having the first wavelength $\lambda_1$ is less than or equal to the first reference intensity, the reflection intensity (or reflectance) of the light beam having the second wavelength $\lambda_2$ is less than or equal to the second reference intensity, . . . and the reflection intensity (or reflectance) of the light beam having the $n^{th}$ wavelength $\lambda_n$ is less than or equal to the $n^{th}$ reference intensity, the controller 130 may determine that the food has been rotten.

The controller 130 may calculate a distance from the electronic apparatus 100 to the object O. The controller 130 may measure the distance from the electronic apparatus 100 to the object O based on a time difference between a time at which the light-emitting diode array 111 transmits a light beam and a time at which the photodiode 121 receives the light beam and based on the speed of light (about 300,000,000 m/s).

The controller 130 may calculate a distance from the electronic apparatus 100 to the object O at different times.

The controller 130 may identify a degree of rottenness of a food or cooking information of the food based on a change in distance from the electronic apparatus 100 to the object O according to a time. In general, it is known that a volume of a food is reduced due to moisture being evaporated as the food is rotten or cooked.

When an increased value of the distance from the electronic apparatus 100 to the object O is greater than or equal to a first reference distance and a change rate of the distance from the electronic apparatus 100 to the object O is less than or equal to a second reference distance, the controller 130 may determine that the food has been rotten or the cooking of the food has been completed.

The display 190 may display information (for example, an image and/or message) about a state of the object in response to a display signal of the controller 130. For example, the display 190 may display an image and/or message indicating rottenness of a food or may display an image and/or message indicating the completion of cooking of the food.

The display 190 may include a light-emitting diode (LED) panel, an organic light-emitting diode (OLED) panel, a liquid crystal display (LCD) panel, or the like.

Figure 7:
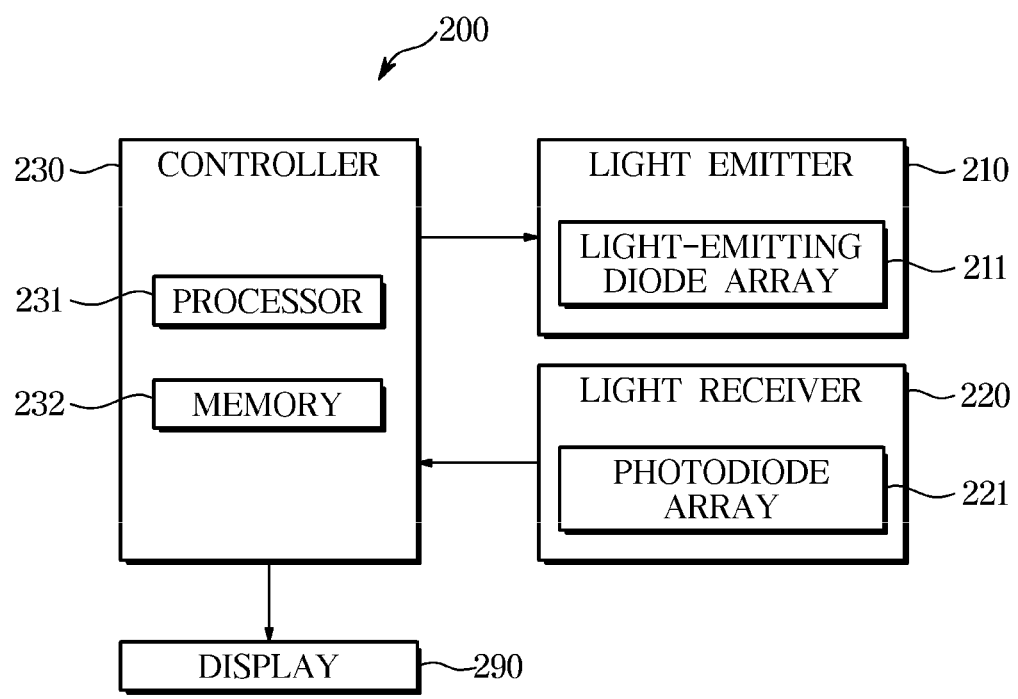
FIG. 7 is a view illustrating a configuration of an electronic apparatus according to one embodiment.
Figure 8:
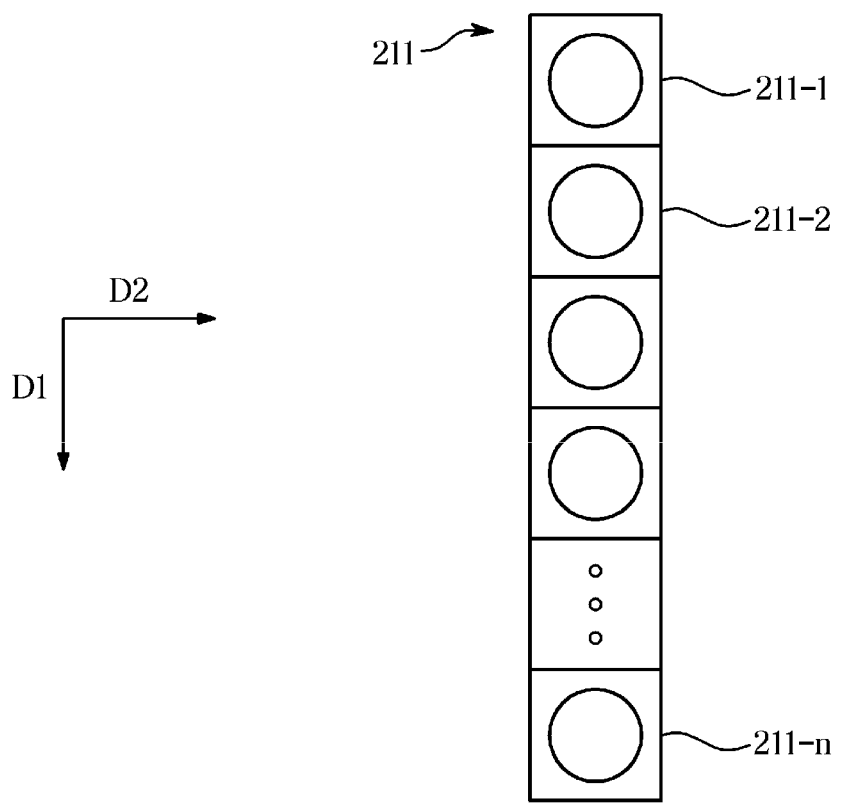
FIG. 8 shows views illustrating a light-emitting diode array and a photodiode array included in the electronic apparatus according to one embodiment.
Figure 8:
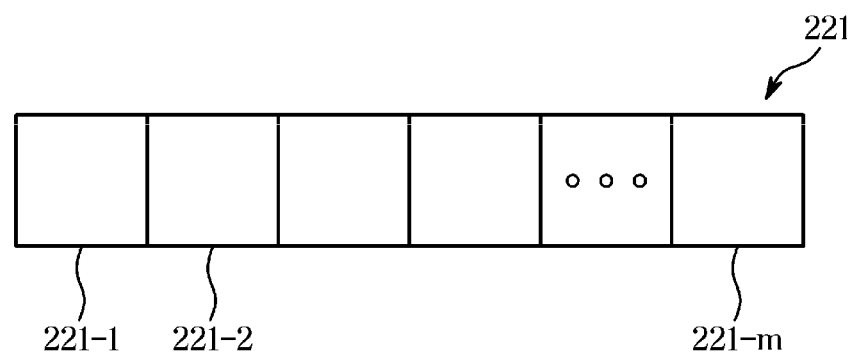
Figure 9:
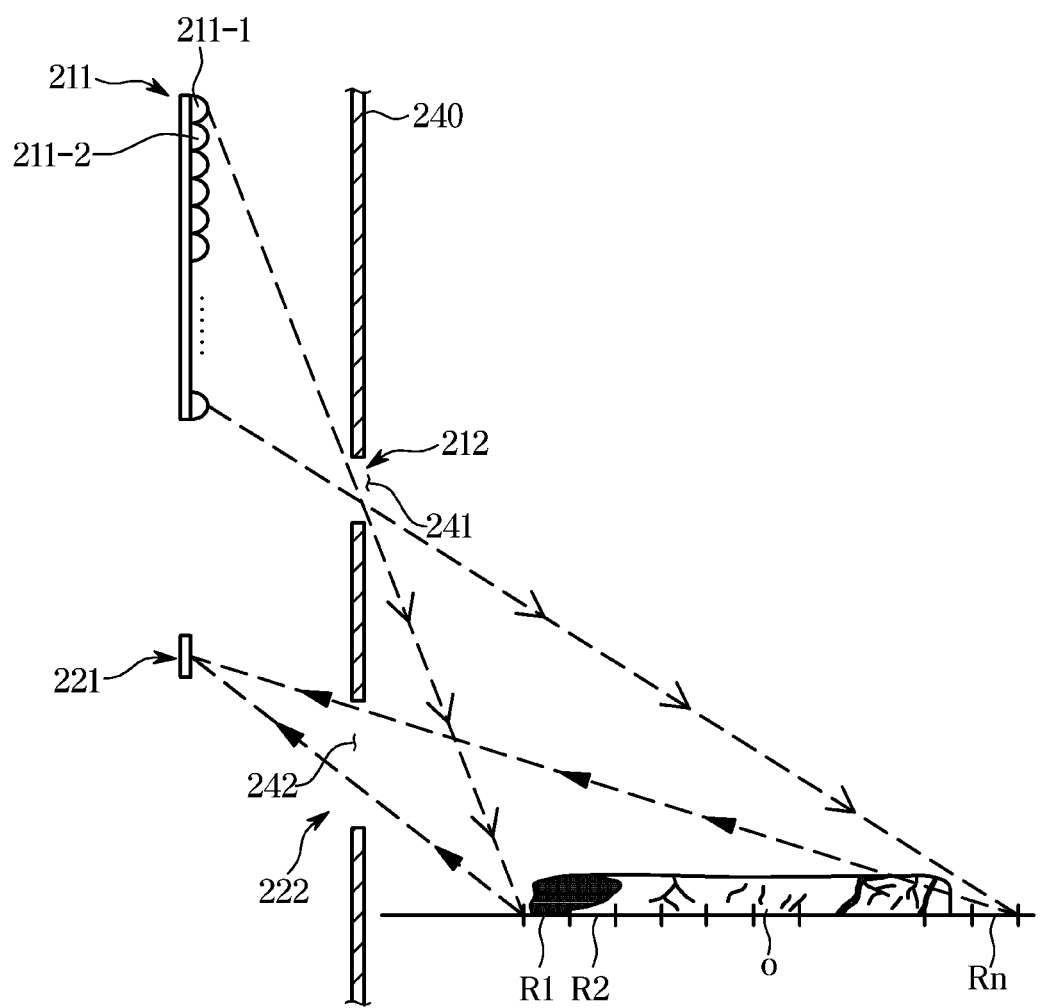
FIG. 9 shows side views illustrating the light-emitting diode array and the photodiode array included in the electronic apparatus according to one embodiment.
Figure 10:
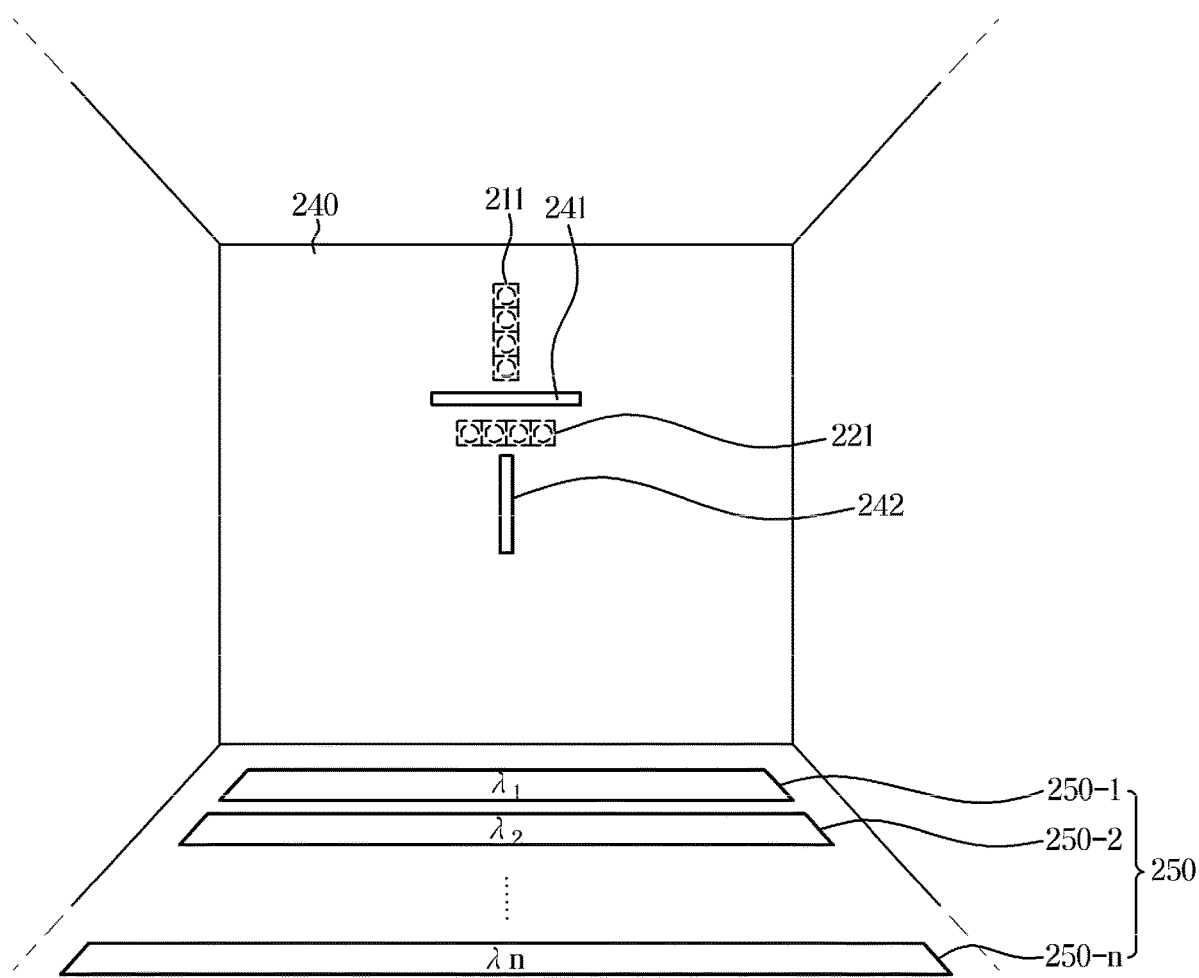
FIG. 10 is a view illustrating a light spot formed by a light beam transmitted from a first light-emitting diode included in the electronic apparatus according to one embodiment.
Figure 11:
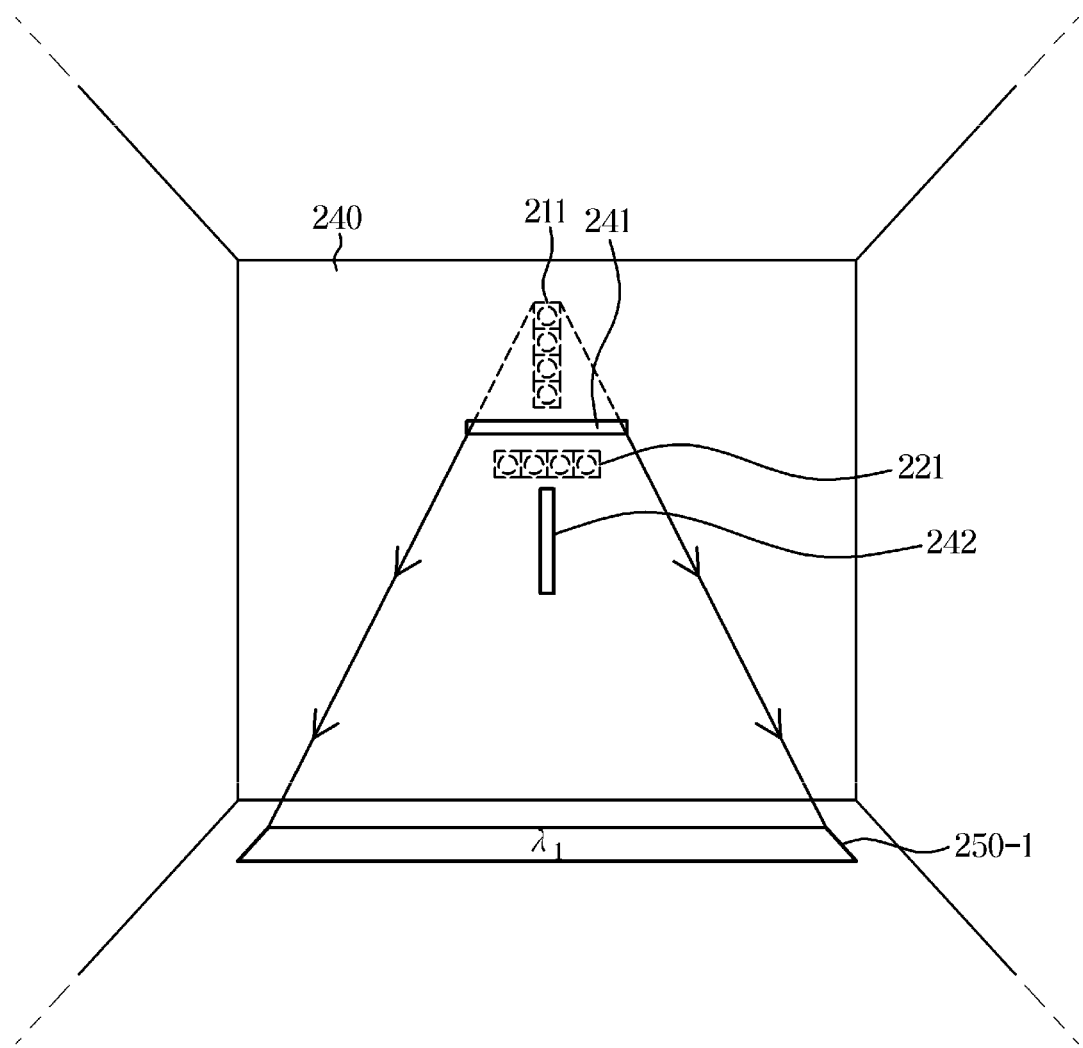
FIG. 11 is a view illustrating light spots formed by light beams transmitted from a plurality of light-emitting diodes included in the electronic apparatus according to one embodiment.
Figure 12:
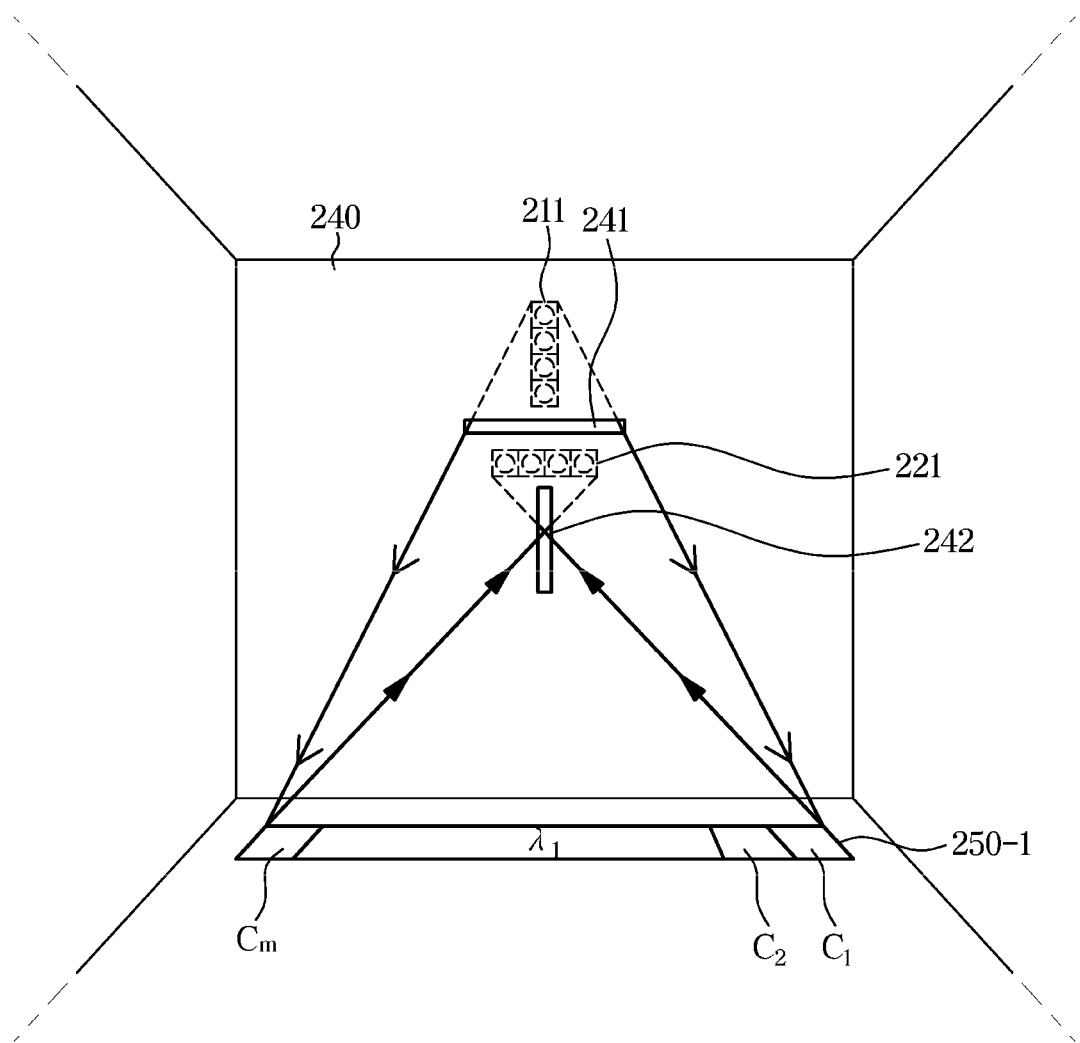
FIG. 12 is a view illustrating that the electronic apparatus according to one embodiment receives a light beam reflected on an object.
Figure 13:
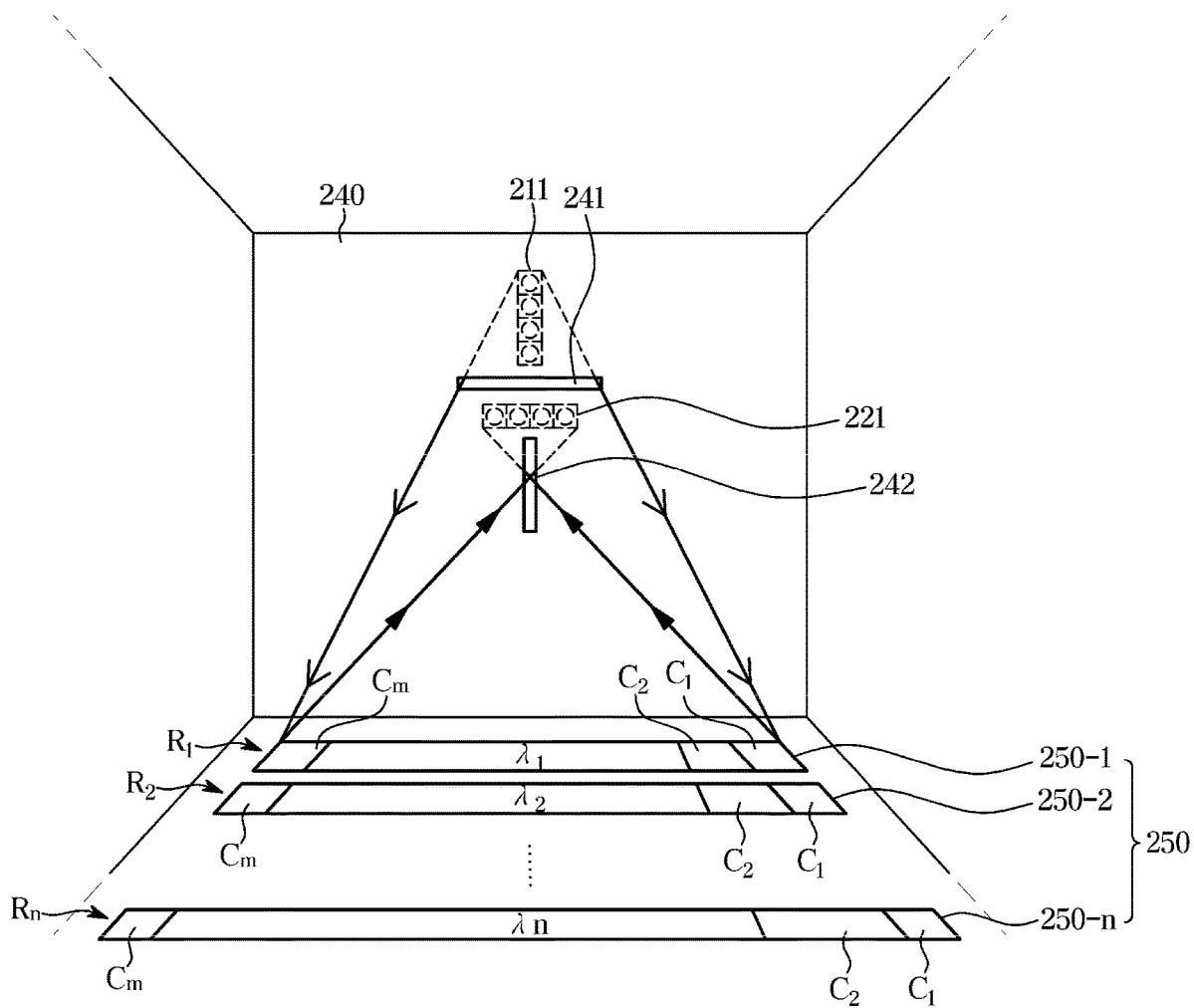
FIG. 13 is a view illustrating a traveling path of a light beam transmitted from the electronic apparatus according to one embodiment.

FIG. 7 is a view illustrating a configuration of an electronic apparatus according to one embodiment. FIG. 8 shows views illustrating a light-emitting diode array and a photodiode array included in the electronic apparatus according to one embodiment. FIG. 9 shows side views illustrating the light-emitting diode array and the photodiode array included in the electronic apparatus according to one embodiment. FIG. 10 is a view illustrating a light spot formed by a light beam transmitted from a first light-emitting diode included in the electronic apparatus according to one embodiment. FIG. 11 is a view illustrating light spots formed by light beams transmitted from a plurality of light-emitting diodes included in the electronic apparatus according to one embodiment. FIG. 12 is a view illustrating that the electronic apparatus according to one embodiment receives a light beam reflected on an object. FIG. 13 is a view illustrating a traveling path of a light beam transmitted from the electronic apparatus according to one embodiment.

Referring to FIGS. 7, 8, 9, 10, 11, 12, and 13, an electronic apparatus 200 includes a light emitter 210 capable of transmitting a plurality of light beams having different wavelengths toward an object, a light receiver 220 capable of receiving light beams, a controller 230 configured to control the light emitter 210, process a signal output from the light receiver 220, and identify a state of the object, and a display 290 configured to display information about the state of the object.

The light emitter 210 includes a light-emitting diode array 211 capable of transmitting a plurality of light beams having different wavelengths. As shown in FIG. 8, the light-emitting diode array 211 includes a first light-emitting diode 211-1, a second light-emitting diode 211-2, . . . and an $n^{th}$ light-emitting diode 211-$n$. The first light-emitting diode 211-1, the second light-emitting diode 211-2, . . . and the $n^{th}$ light-emitting diode 211-$n$ may be disposed in a line in a first direction D1.

The first light-emitting diode 211-1, the second light-emitting diode 211-2, . . . and the $n^{th}$ light-emitting diode 211-$n$ may transmit light beams having different wavelengths. For example, the first light-emitting diode 211-1 may transmit a light beam having a first wavelength $\lambda_1$, and the second light-emitting diode 211-2 may transmit a light beam having a second wavelength $\lambda_2$. In addition, the $n^{th}$ light-emitting diode 211-$n$ may transmit a light beam having an $n^{th}$ wavelength $\lambda_n$.

The light-emitting diode array 211 including the first light-emitting diode 211-1, the second light-emitting diode 211-2, . . . and the $n^{th}$ light-emitting diode 211-$n$ may sequentially transmit the light beam having the first wavelength $\lambda_1$, the light beam having the second wavelength $\lambda_2$, . . . and the light beam having the $n^{th}$ wavelength $\lambda_n$ in response to an emission control signal of the controller 230.

The light receiver 220 includes a photodiode array 221 capable of receiving light beams. The photodiode array 221 includes a first photodiode 221-1, a second photodiode 221-2, . . . and an $m^{th}$ photodiode 221-$m$.

As shown in FIG. 8, the first photodiode 221-1, the second photodiode 221-2, . . . and the $m^{th}$ photodiode 221-$m$ may be disposed in a line in a second direction D2. The second direction D2 may be orthogonal to the first direction D1. In other words, a direction in which a plurality of photodiodes 221-1, 221-2, . . . and 221-$m$ are disposed may be orthogonal to a direction in which a plurality of light-emitting diodes 211-1, 211-2, . . . and 211-$n$ are disposed.

All of the first photodiode 221-1, the second photodiode 221-2, . . . and the $m^{th}$ photodiode 221-$m$ may receive light beams having various wavelengths and may measure intensities of the received light beams. For example, all of the first photodiode 221-1, the second photodiode 221-2, . . . and the $m^{th}$ photodiode 221-$m$ may receive the light beam having the first wavelength $\lambda_1$, the light beam having the second wavelength $\lambda_2$, . . . and the light beam having the $n^{th}$ wavelength $\lambda_n$ and may output reception intensity signals corresponding to intensities of the received light beams.

The photodiode array 221 may receive a light beam that is transmitted from the light-emitting diode array 211 and is reflected on an object O and may transmit an electrical signal corresponding to intensity of the received light beam to the controller 230.

A first optical member 212 configured to guide a light beam to the object O is provided at a side through which a light beam is transmitted from the light-emitting diode array 211. The first optical member 212 may guide light beams transmitted from the plurality of light-emitting diodes 211-1, 211-2, . . . and 211-$n$ constituting the light-emitting diode array 211 toward the object O.

As shown in FIGS. 9 and 10, the first optical member 212 may include a light blocking plate 240 in which a first slit 241 is formed, the first slit 241 guiding the light beams transmitted from the plurality of light-emitting diodes 211-1, 211-2, . . . and 211-$n$ to the object O.

The first slit 241 may be formed in the light blocking plate 240 so as to be elongated in the second direction D2. The second direction D2 may be orthogonal to the first direction D1 in which the plurality of light-emitting diodes 211-1, 211-2, . . . and 211-$n$ are disposed.

Since the plurality of light-emitting diodes 211-1, 211-2, . . . and 211-$n$ are disposed in the first direction D1 and the first slit 241 is formed to be elongated in the second direction D2, as shown in FIG. 9, the light beams transmitted from the plurality of light-emitting diodes 211-1, 211-2, . . . and 211-$n$ may be projected at different positions of the object O.

For example, the light beam transmitted from the first light-emitting diode 211-1 disposed farthest from the first slit 241 may be projected at a position of a first row $R_1$ closest to the light blocking plate 240. In addition, the light beam transmitted from the second light-emitting diode 211-2 may be projected at a position of a second row $R_2$, and the second row $R_2$ may be positioned farther away from the light blocking plate 240 than the first row $R_1$. The light beam transmitted from the $n^{th}$ light-emitting diode 211-$n$ disposed at a position closest to the first slit 241 may be projected at a position of an $n^{th}$ row $R_n$, and the $n^{th}$ row $R_n$ may be positioned farthest from the light blocking plate 240.

Since the plurality of light-emitting diodes 211-1, 211-2, . . . and 211-$n$ are disposed in the first direction D1 and the first slit 241 is formed to be elongated in the second direction D2, as shown in FIG. 10, the light beams transmitted from the plurality of light-emitting diodes 211-1, 211-2, . . . and 211-$n$ may extend in the second direction D2 and a direction opposite to the second direction D2.

As shown in FIG. 11, the light beams transmitted from the plurality of light-emitting diodes 211-1, 211-2, . . . and 211-$n$ may form a plurality of light spots 250 having a band shape. For example, the light beam transmitted from the first light-emitting diode 211-1 may form a first light spot 250-1 of the light beam having the first wavelength $\lambda_1$, and the light beam transmitted from the second light-emitting diode 211-2 may form a second light spot 250-2 of the light beam having the second wavelength $\lambda_2$. In addition, the light beam transmitted from the $n^{th}$ light-emitting diode 211-$n$ may form an $n^{th}$ light spot 250-$n$ of the light beam having the $n^{th}$ wavelength $\lambda_n$.

A second optical member 222 configured to guide a light beam to the photodiode array 221 is provided at a side through which a light beam is received by the photodiode array 221. The second optical member 222 may guide light beams reflected on the object O toward the plurality of photodiodes 221-1, 221-2, . . . and 221-$m$ constituting the photodiode array 221.

As shown in FIG. 12, the second optical member 222 may include a light blocking plate 240 in which a second slit 242 is formed, the second slit 242 guiding the light beams reflected on the object O to the plurality of photodiodes 221-1, 221-2, . . . and 221-$m$.

The second slit 242 may be formed in the light blocking plate 240 so as to be elongated in the first direction D1. The first direction D1 may be orthogonal to the second direction D2 in which the plurality of photodiodes 221-1, 221-2, . . . and 221-m are disposed.

As shown in FIG. 12, a light beam projected on the object O may form a light spot having a band shape extending in the second direction D2. A light beam reflected from the light spot having the band shape may pass through the second slit 242 and may be incident on the plurality of photodiodes 221-1, 221-2, . . . 221-m.

Light beams reflected at different positions of a light spot may be incident on different photodiodes of the plurality of photodiodes 221-1, 221-2, . . . and 221-m.

For example, as shown in FIG. 12, a light beam reflected at a position of a first column $C_1$ positioned at a rightmost side of the light spot may pass through the second slit 242 and may be incident on the first photodiode 221-1 positioned at a leftmost side. A light beam reflected at a position of a second column $C_2$ positioned more to the left than the position of the first column $C_1$ may pass through the second slit 242 and may be incident on the second photodiode 221-2 positioned more to the right than the first photodiode 221-1. In addition, a light beam reflected at a position of an $m^{th}$ column $C_m$ positioned at a leftmost side of the light spot may pass through the second slit 242 and may be incident on the $m^{th}$ photodiode 221-m positioned at a rightmost side.

As shown in FIG. 13, the light beams transmitted from the plurality of light-emitting diodes 211-1, 211-2, . . . and 211-n may be projected at different positions (different positions in a vertical direction in FIG. 13) and may form light spots 250 having a band shape. In addition, light beams reflected at different positions (different positions in a horizontal direction in FIG. 13) of the light spots 250 may be incident on different photodiodes.

For example, the light beam having the first wavelength Ai transmitted from the first light-emitting diode 211-1 may form a first light spot 250-1 at a position of a first row $R_1$. A light beam reflected at a position of a first column $C_1$ of the first light spot 250-1 may be incident on the first photodiode 221-1, and a light beam reflected at a position of a second column $C_2$ of the first light spot 250-1 may be incident on the second photodiode 221-2. In addition, a light beam reflected at a position of an $m^{th}$ column $C_m$ of the first light spot 250-1 may be incident on the $m^{th}$ photodiode 221-m.

The light beam having the second wavelength $\lambda_2$ transmitted from the second light-emitting diode 211-2 may form a second light spot 250-2 at a position of a second row $R_2$. A light beam reflected at a position of a first column $C_1$ of the second light spot 250-2 may be incident on the first photodiode 221-1, and a light beam reflected at a position of a second column $C_2$ of the second light spot 250-2 may be incident on the second photodiode 221-2. In addition, a light beam reflected at a position of an $m^{th}$ column Cm of the second light spot 250-2 may be incident on the $m^{th}$ photodiode 221-m.

The light beam having the $n^{th}$ wavelength $\lambda_n$ transmitted from the $n^{th}$ light-emitting diode 211-n may form an $n^{th}$ light spot 250-n at a position of an $n^{th}$ row $R_n$. A light beam reflected at a position of a first column $C_1$ of the $n^{th}$ light spot 250-n may be incident on the first photodiode 221-1, and a light beam reflected at a position of a second column $C_2$ of the $n^{th}$ light spot 250-n may be incident on the second photodiode 221-2. In addition, a light beam reflected at a position of an $m^{th}$ column $C_m$ of the $n^{th}$ light spot 250-n may be incident on the $m^{th}$ photodiode 221-m.

As described above, light spots in the same row may be formed by light beams having the same wavelength transmitted from the same light-emitting diode, and light beams reflected at the positions of the same column may be incident on the same photodiode.

The controller 230 may be electrically connected to the light emitter 210 and the light receiver 220. For example, the controller 230 may output an emission control signal to the light-emitting diode array 211 and may receive a reception intensity signal from the photodiode array 221.

The controller 230 includes a processor 231 and a memory 232.

The processor 231 may generate emission control signals for sequentially turning on the plurality of light-emitting diodes 211-1, 211-2, . . . and 211-n included in the light-emitting diode array 211. In addition, the processor 231 may sequentially store reception intensities (reflection intensities) received by the plurality of photodiodes 221-1, 221-2, . . . and 221-m included in the photodiode array 221 in the memory 232. The processor 231 may sequentially store reflection intensity (or reflectance) of the light beam having the first wavelength $\lambda_1$, reflection intensity (or reflectance) of the light beam having the second wavelength $\lambda_2$, . . . and reflection intensity (reflectance) of the light beam having the $n^{th}$ wavelength $\lambda_n$ in the memory 232.

The controller 230 may identify the object O based on the reflection intensity (or reflectance) of the light beam having the first wavelength $\lambda_1$, the reflection intensity (or reflectance) of the light beam having the second wavelength $\lambda_2$, . . . and the reflection intensity (reflectance) of the light beam having the $n^{th}$ wavelength $\lambda_n$.

The controller 230 may calculate a rottenness value y of a food and/or a cooking value of the food by respectively inputting measured reflection intensity of the light beam having the first wavelength $\lambda_1$, measured reflection intensity of the light beam having the second wavelength $\lambda_2$, . . . and measured reflection intensity of the light beam having the $n^{th}$ wavelength $\lambda_n$ in $x_1, x_2, \ldots$ and $x_n$ of Expression 1.

The controller 230 may identify a degree of rottenness of a food or a degree of cooking of the food based on a change in reflection intensity (or reflectance) of the light beam having the first wavelength $\lambda_1$, a change in reflection intensity (or reflectance) of the light beam having the second wavelength $\lambda_2$, . . . and a change in reflection intensity (reflectance) of the light beam having the $n^{th}$ wavelength $\lambda_n$.

The controller 230 may calculate a distance from the electronic apparatus 200 to the object O based on a time difference between a time at which the light-emitting diode array 211 transmits a light beam and a time at which the photodiode array 221 receives the light beam and based on the speed of light. The controller 230 may identify a degree of rottenness of a food or a degree of cooking of the food based on the distance from the electronic apparatus 200 to the object O and a change in the distance.

The display 290 may display information (for example, an image and/or message) about a state of the object in response to a display signal of the controller 230. For example, the display 290 may display an image and/or message indicating rottenness of a food or may display an image and/or message indicating completion of cooking of the food.

As described above, the electronic apparatus 200 including the light-emitting diode array 211 and the photodiode array 221 may irradiate light beams having different wavelengths onto an entire surface of the object O rather than a portion of the object O and may measure reflection intensities (or reflectances) of the light beams having the different wavelengths. Accordingly, the electronic apparatus 200 may more accurately identify the object O and may identify a degree of rottenness of a food or a degree of cooking of the food.

Figure 14:
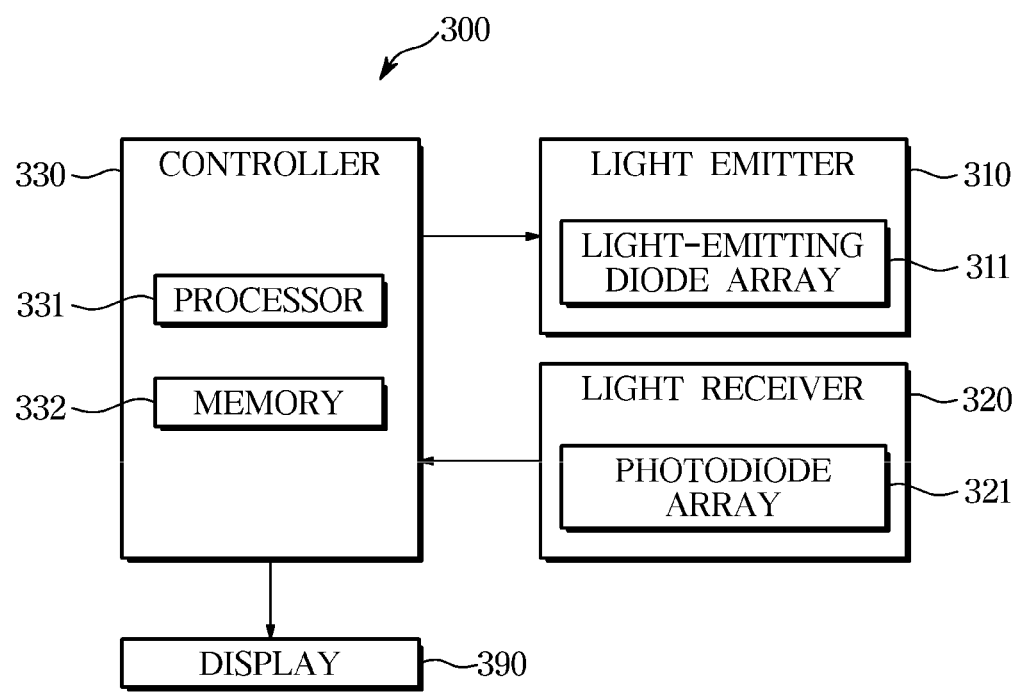
FIG. 14 is a view illustrating a configuration of an electronic apparatus according to one embodiment.
Figure 15:
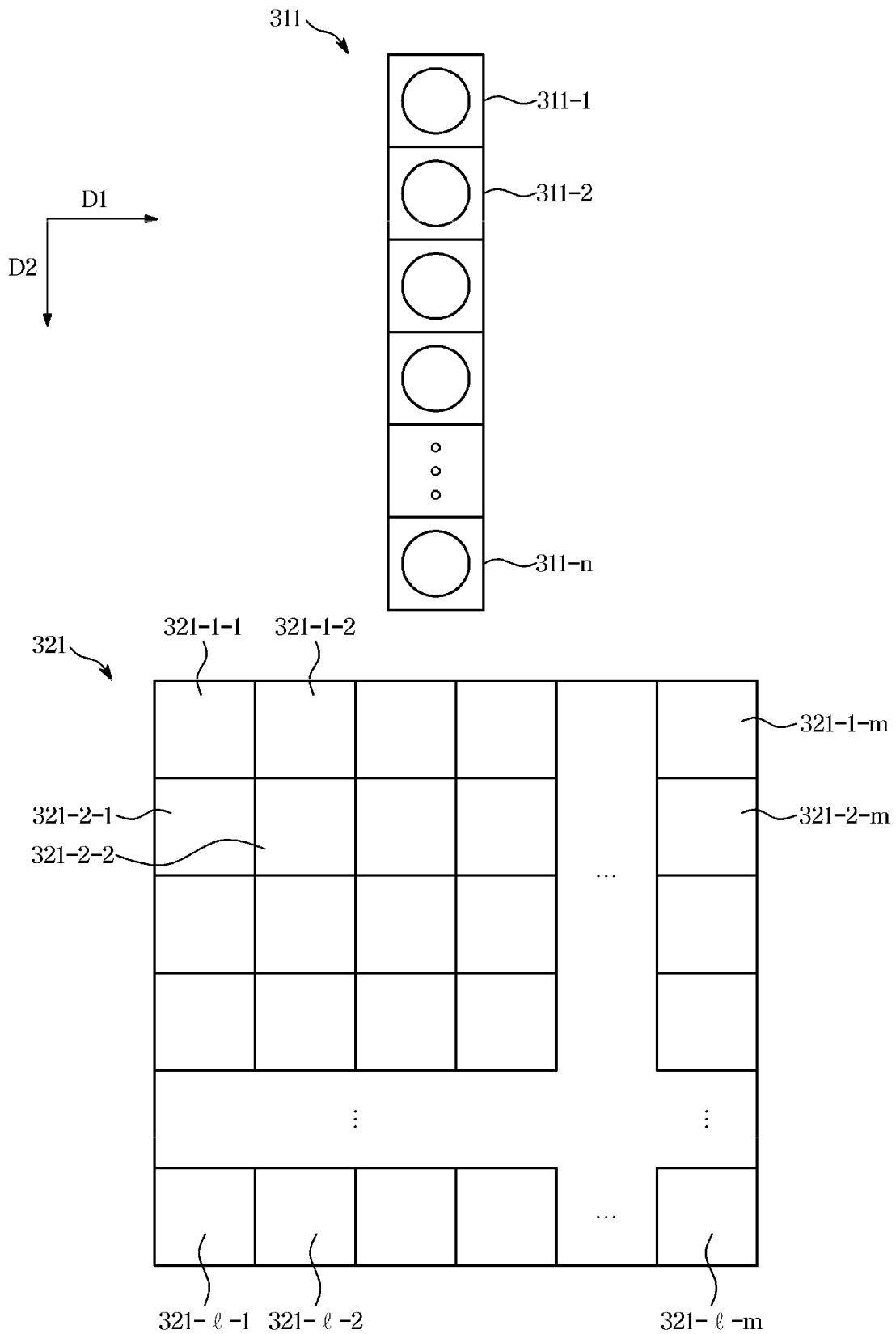
FIG. 15 shows views illustrating a light-emitting diode array and a photodiode array included in the electronic apparatus according to one embodiment.
Figure 16:
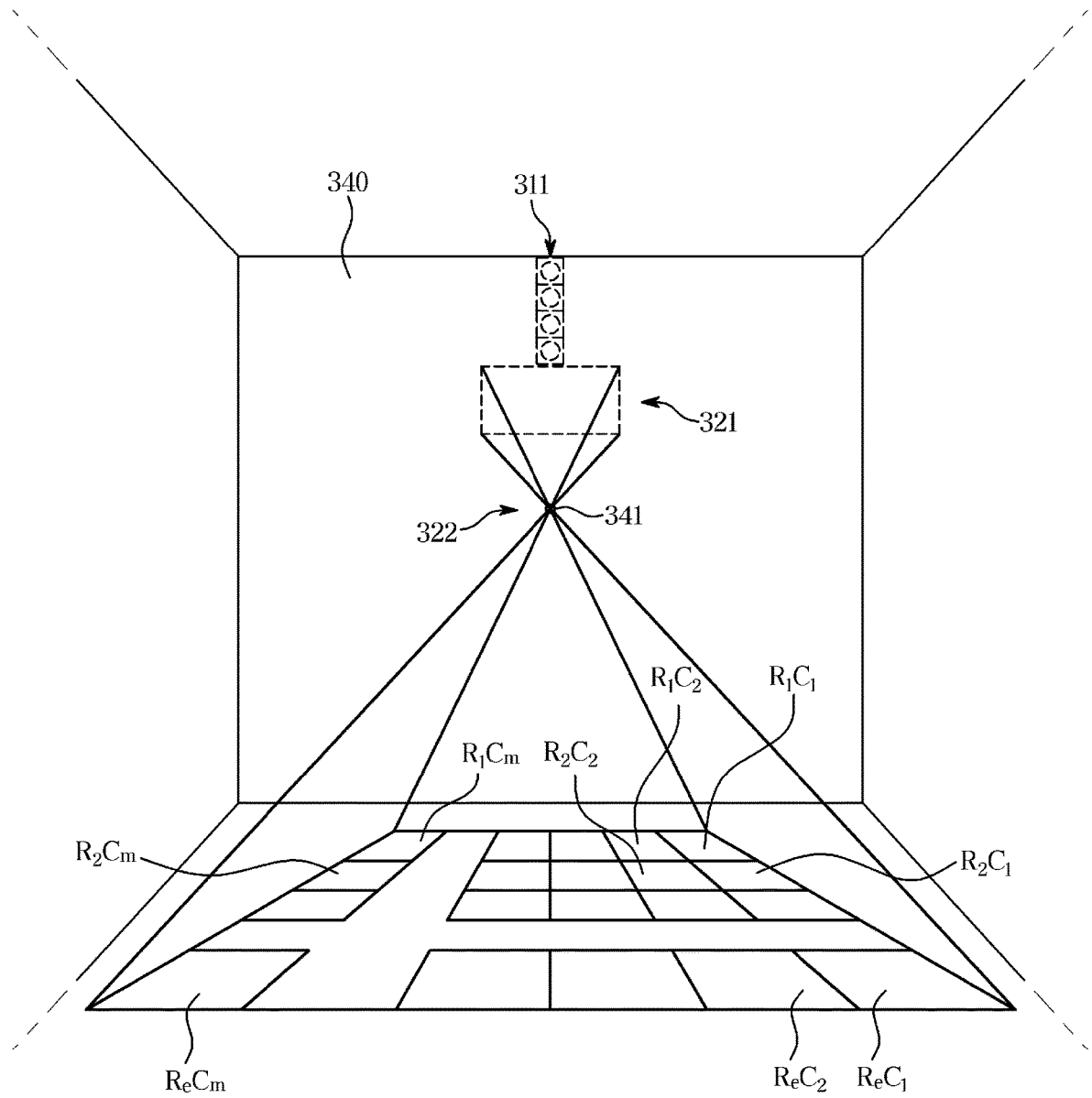
FIG. 16 is a view illustrating a traveling path of a light beam transmitted from the electronic apparatus according to one embodiment.
Figure 17:
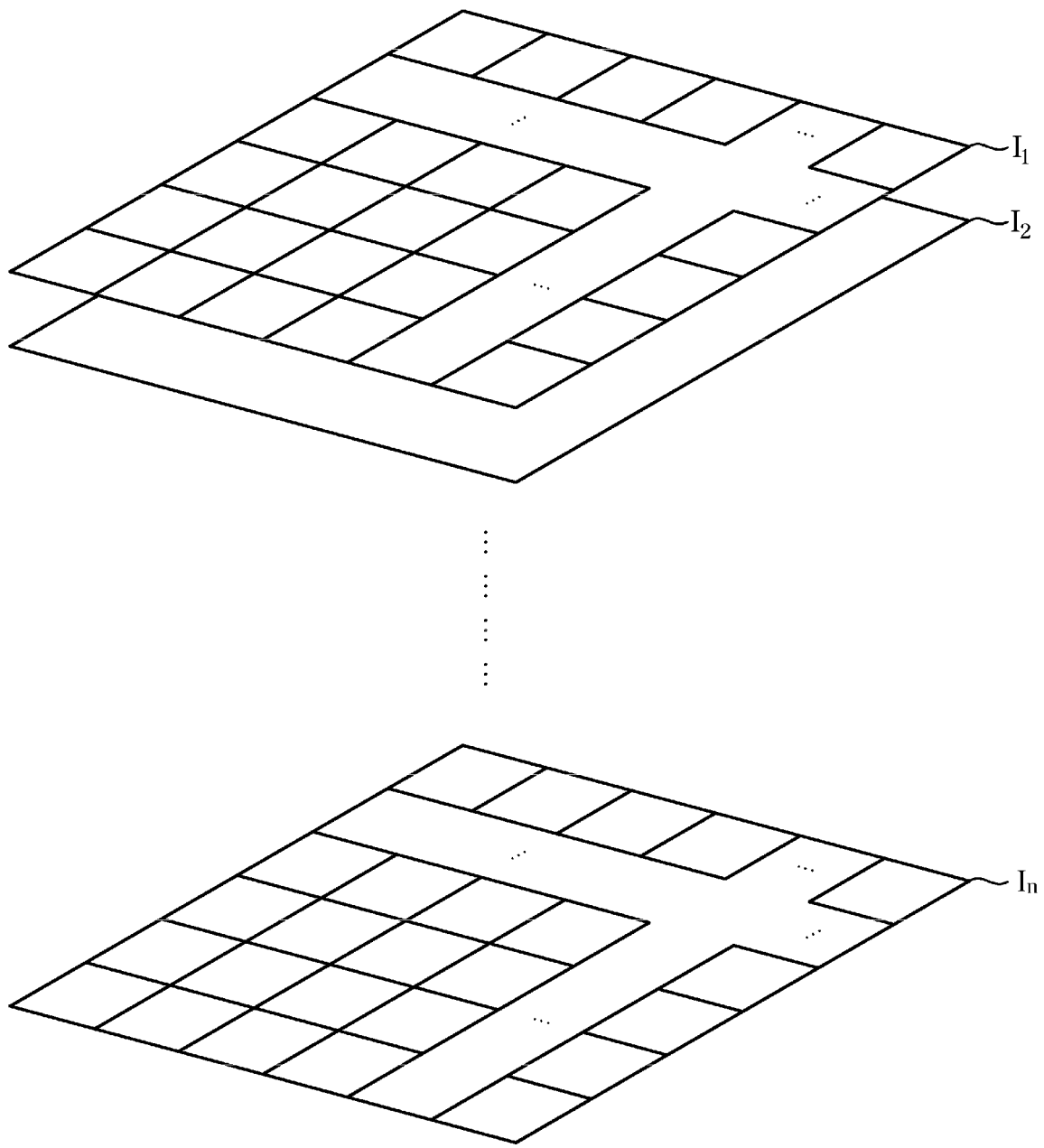
FIG. 17 shows image data captured by the electronic apparatus according to one embodiment.

FIG. 14 is a view illustrating a configuration of an electronic apparatus according to one embodiment. FIG. 15 shows views illustrating a light-emitting diode array and a photodiode array included in the electronic apparatus according to one embodiment. FIG. 16 is a view illustrating a traveling path of a light beam transmitted from the electronic apparatus according to one embodiment. FIG. 17 shows image data captured by the electronic apparatus according to one embodiment.

Referring to FIGS. 14, 15, 16, and 17, an electronic apparatus 300 includes a light emitter 310 capable of transmitting a plurality of light beams having different wavelengths toward an object, a light receiver 320 capable of receiving light beams, a controller 330 configured to control the light emitter 310, process a signal output from the light receiver 320, and identify a state of the object, and a display 390 configured to display information about the state of the object.

The light emitter 310 includes a light-emitting diode array 311 capable of transmitting a plurality of light beams having different wavelengths.

The light-emitting diode array 311 includes a first light-emitting diode 311-1, a second light-emitting diode 311-2, ... and an $n^{th}$ light-emitting diode 311-$n$, which are capable of transmitting a plurality of light beams having different wavelengths. The first light-emitting diode 311-1 may transmit a light beam having a first wavelength $\lambda_1$, and the second light-emitting diode 311-2 may transmit a light beam having a second wavelength $\lambda_2$. In addition, the $n^{th}$ light-emitting diode 311-$n$ may transmit a light beam having an $n^{th}$ wavelength $\lambda_n$.

The first light-emitting diode 311-1, the second light-emitting diode 311-2, ... and the $n^{th}$ light-emitting diode 311-$n$ may be disposed in a line. However, the present disclosure is not limited thereto. A plurality of light-emitting diodes 311-1, 311-2, ... and 311-$n$ may be variously disposed. For example, the plurality of light-emitting diodes 311-1, 311-2, ... and 311-$n$ may be disposed in columns and rows.

The light-emitting diode array 311 including the first light-emitting diode 311-1, the second light-emitting diode 311-2, ... and the $n^{th}$ light-emitting diode 311-$n$ may sequentially transmit the light beam having the first wavelength $\lambda_1$, the light beam having the second wavelength $\lambda_2$, ... and the light beam having the $n^{th}$ wavelength $\lambda_n$ in response to an emission control signal of the controller 330.

The light receiver 320 includes a photodiode array 321 capable of receiving light beams.

According to another aspect, in comparison to FIG. 7, FIG. 14 illustrates the photodiode array 321 includes a 1-$1^{st}$ photodiode 321-1-1, a 1-$2^{nd}$ photodiode 321-1-2, ... and a 1-m$^{th}$ photodiode 321-1-$m$, a 2-$1^{st}$ photodiode 321-2-1, a 2-$2^{nd}$ photodiode 321-2-2, ... and a 2-m$^{th}$ photodiode 321-2-$m$, ... and an 1-$1^{st}$ photodiode 321-$l$-1, an 1-$2^{nd}$ photodiode 321-$l$-2, ... and an l-m$^{th}$ photodiode 321-$l$-$m$.

As shown in FIG. 15, a plurality of photodiodes 321-1-1 to 32-$l$-$m$ may be disposed in a matrix form in rows and columns. The plurality of photodiodes 321-1-1 to 32-$l$-$m$ may form a plurality of rows in a first direction D1 and may form a plurality of columns in a second direction D2.

The 1-$1^{st}$ photodiode 321-1-1, the 1-$2^{nd}$ photodiode 321-1-2, ... and the 1-m$^{th}$ photodiode 321-1-$m$ may be disposed in a first row, and the 2-$1^{st}$ photodiode 321-2-1, the 2-$2^{nd}$ photodiode 321-2-2, ... and the 2-m$^{th}$ photodiode 321-2-$m$ may be disposed in a second row. In addition, the 1-$1^{st}$ photodiode 321-$l$-1, the 1-$2^{nd}$ photodiode 321-$l$-2, ... and the l-m$^{th}$ photodiode 321-1-$m$ may be disposed in an $l^{th}$ row.

The photodiode array 321 may receive a light beam that is transmitted from the light-emitting diode array 311 and is reflected on an object O and may transmit a reception intensity signal corresponding to intensity of the received light beam to the controller 330.

An optical member 322 configured to guide a light beam to the photodiode array 321 may be provided at a side through which a light beam is received by the photodiode array 321. The optical member 322 may guide light beams reflected on the object O toward the plurality of photodiodes 321-1-1 to 321-$l$-$m$ constituting the photodiode array 321.

As shown in FIG. 16, the optical member 322 may include a light blocking plate 340 in which an aperture 341 is formed, the aperture 341 guiding the light beams reflected on the object O to the plurality of photodiodes 321-1-1 to 321-$l$-$m$.

Light beams projected on the object O may be reflected on the object O, and the reflected light beams may pass through the aperture 341 and be incident on the plurality of photodiodes 321-1-1 to 321-$l$-$m$.

Light beams reflected at different positions of the object O may be incident on different photodiodes of the plurality of photodiodes 321-1-1 to 321-$l$-$m$. For example, as shown in FIG. 16, a light beam reflected at a position of a first row $R_1$ and a first column $C_1$ of the object O may pass through the aperture 341 and may be incident on the 1-$1^{st}$ photodiode 321-1-1. A light beam reflected at a position of the first row $R_1$ and a second column $C_2$ may pass through the aperture 341 and may be incident on the 1-$2^{nd}$ photodiode 321-1-2. In addition, a light beam reflected at a position of the first row $R_1$ and an m$^{th}$ column $C_m$ may pass through the aperture 341 and may be incident on the 1-m$^{th}$ photodiode 321-1-$m$. A light beam reflected at a position of an $l^{th}$ row $R_1$ and the m$^{th}$ column $C_m$ may pass through the aperture 341 and may be incident on the l-m$^{th}$ photodiode 321-$l$-$m$.

As described above, among light beams transmitted from the light-emitting diode array 311, a light beam projected in a specific region may pass through the aperture 341 and may be incident on the photodiode array 321. Since the photodiode array 321 includes the plurality of photodiodes 321-1-1 to 321-$l$-$m$ disposed in a matrix form in rows and columns, as shown in FIG. 16, a specific region detectable by the photodiode array 321 may have an approximately quadrangular shape. In addition, light beams received by the plurality of photodiodes 321-1-1 to 321-$l$-$m$ constituting the photodiode array 321 may form a two-dimensional image.

All of the plurality of photodiodes 321-1-1 to 321-$l$-$m$ constituting the photodiode array 321 may receive light beams having various wavelengths and may measure intensities of the received light beams. For example, all of the plurality of photodiodes 321-1-1 to 321-$l$-$m$ may receive the light beam having the first wavelength $\lambda_1$, the light beam having the second wavelength $\lambda_2$, ... and the light beam having the $n^{th}$ wavelength $\lambda_n$ and may output reception intensity signals corresponding to intensities of the received light beams.

When the light-emitting diode array 311 transmits the light beam having the first wavelength $\lambda_1$, the photodiode array 321 may receive the light beam having the first wavelength $\lambda_1$ reflected on the object O and may measure reflection intensity of the light beam having the first wavelength $\lambda_1$. In addition, the reflection intensity of the light beam having the first wavelength $\lambda_1$ measured by the plurality of photodiodes 321-1-1 to 321-*l*-*m* may form a first image $l_1$ by the light beam having the first wavelength $\lambda_1$ as shown in FIG. 17.

When the light-emitting diode array 311 transmits the light beam having the second wavelength $\lambda_2$, the photodiode array 321 may receive the light beam having the second wavelength $\lambda_2$ reflected on the object O and may measure reflection intensity of the light beam having the second wavelength $\lambda_2$. In addition, the reflection intensity of the light beam having the second wavelength $\lambda_2$ measured by the plurality of photodiodes 321-1-1 to 321-*l*-*m* may form a second image $l_2$ by the light beam having the second wavelength $\lambda_2$ as shown in FIG. 17.

In the same manner, when the light-emitting diode array 311 transmits the light beam having the $n^{th}$ wavelength $\lambda_n$, the photodiode array 321 may receive the light beam having the $n^{th}$ wavelength $\lambda_n$ reflected on the object O and may measure reflection intensity of the light beam having the $n^{th}$ wavelength $\lambda_n$. In addition, the reflection intensity of the light beam having the $n^{th}$ wavelength $\lambda_n$ measured by the plurality of photodiodes 321-1-1 to 321-*l*-*m* may form an $n^{th}$ image $l_n$ by the light beam having the $n^{th}$ wavelength $\lambda_n$ as shown in FIG. 17.

The controller 330 may be electrically connected to the light emitter 310 and the light receiver 320. For example, the controller 330 may output an emission control signal to the light-emitting diode array 311 and may receive a reception intensity signal from the photodiode array 321.

The controller 330 includes a processor 331 and a memory 332.

The processor 331 may generate emission control signals for sequentially turning on the plurality of light-emitting diodes 311-1, 311-2, ... and 311-*n* included in the light-emitting diode array 311. In addition, the processor 331 may sequentially store reception intensity signals received from the plurality of photodiodes 321-1-1 to 321-*l*-*m* included in the photodiode array 321 in the memory 332. The processor 331 may sequentially store the first image $l_1$ formed by the light beam having the first wavelength $\lambda_1$, the second image $l_2$ formed by the light beam having the second wavelength $\lambda_2$, ... and the $n^{th}$ image $l_n$ formed by the light beam having the $n^{th}$ wavelength $\lambda_n$ in the memory 332.

The controller 330 may identify the object O based on the first image $l_1$ formed by the light beam having the first wavelength $\lambda_1$, the second image $l_2$ formed by the light beam having the second wavelength $\lambda_2$, ... and the $n^{th}$ image $l_n$ formed by the light beam having the $n^{th}$ wavelength $\lambda_n$.

The controller 130 may calculate a rottenness value y of a food and/or a cooking value of the food by respectively inputting measured reflection intensity of the light beam having the first wavelength $\lambda_1$, measured reflection intensity of the light beam having the second wavelength $\lambda_2$, ... and measured reflection intensity of the light beam having the $n^{th}$ wavelength $\lambda_n$ in $x_1, x_2, ...$ and $x_n$ of Expression 1.

The controller 330 may identify a degree of rottenness of a food or a degree of cooking of the food based on a change in the first image $l_1$, a change in the second image $l_2$, ... and a change in the $n^{th}$ image $l_n$.

The controller 330 may calculate a distance from the electronic apparatus 300 to the object O based on a time difference between a time at which the light-emitting diode array 311 transmits a light beam and a time at which the photodiode array 321 receives the light beam and based on the speed of light. The controller 330 may identify a degree of rottenness of a food or a degree of cooking of the food based on the distance from the electronic apparatus 300 to the object O and a change in the distance.

The display 390 may display information (for example, an image and/or message) about a state of the object in response to a display signal of the controller 330. For example, the display 390 may display an image and/or message indicating rottenness of a food or may display an image and/or message indicating completion of cooking of the food.

As described above, the electronic apparatus 300 provided with the light-emitting diode array 311 including n diodes may irradiate light beams having different wavelengths onto an entire surface of the object O rather than a portion of the object. In addition, the electronic apparatus 300 provided with the photodiode array 321 including diodes disposed in an l-by-m matrix may acquire images formed by light beams having different wavelengths. Accordingly, by using the images formed by the light beams having the different wavelengths, the electronic apparatus 300 may more accurately identify the object O and may also identify a degree of rottenness of a food or a degree of cooking of the food.

Figure 18:
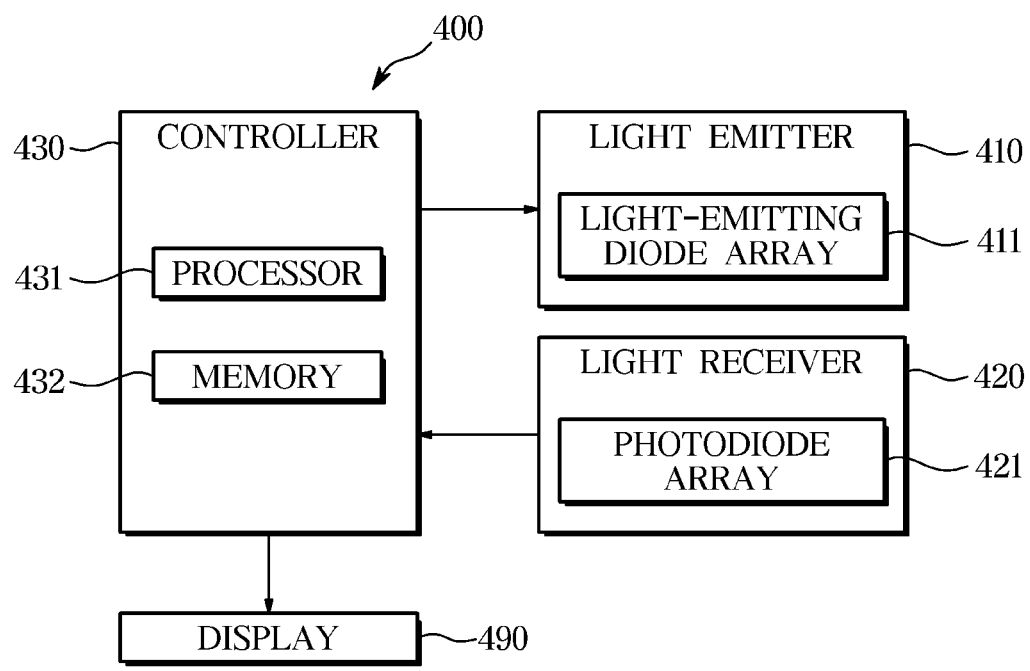
FIG. 18 is a view illustrating a configuration of an electronic apparatus according to one embodiment.
Figure 19:
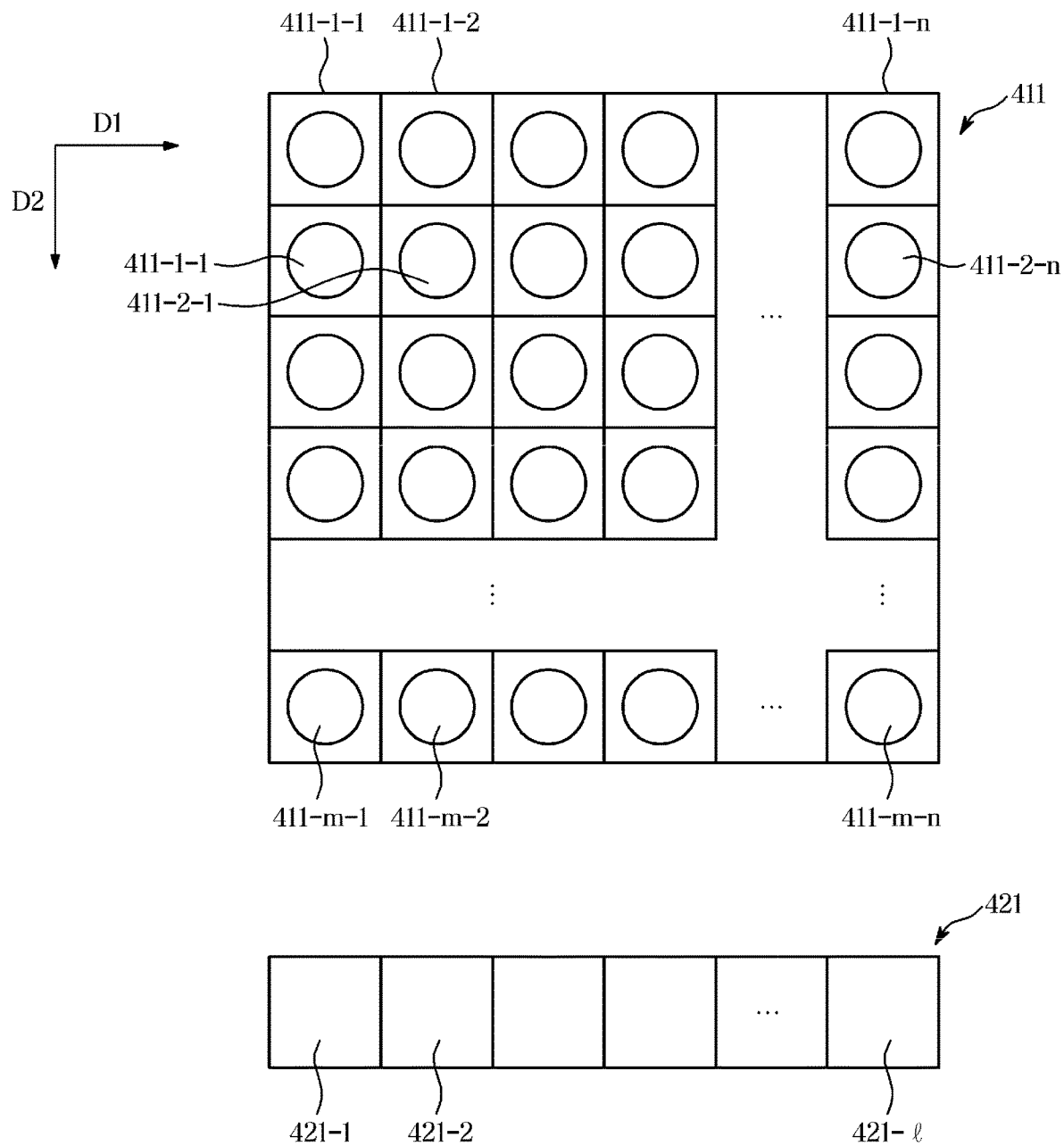
FIG. 19 shows views illustrating a light-emitting diode array and a photodiode array included in the electronic apparatus according to one embodiment.

FIG. 18 is a view illustrating a configuration of an electronic apparatus according to one embodiment. FIG. 19 shows views illustrating a light-emitting diode array and a photodiode array included in the electronic apparatus according to one embodiment.

Referring to FIGS. 18 and 19, an electronic apparatus 400 includes a light emitter 410 capable of transmitting a plurality of light beams having different wavelengths toward an object, a light receiver 420 capable of receiving light beams, a controller 430 configured to control the light emitter 410, process a signal output from the light receiver 420, and identify a state of the object, and a display 490 configured to display information about the state of the object.

The light emitter 410 includes a light-emitting diode array 411 capable of transmitting a plurality of light beams having different wavelengths.

The light-emitting diode array 411 includes a 1-$1^{st}$ light-emitting diode 411-1-1, a 1-$2^{nd}$ light-emitting diode 411-1-2, ... and a 1-$n^{th}$ light-emitting diode 411-1-*n*, a 2-$1^{st}$ light-emitting diode 411-2-1, a 2-$2^{nd}$ light-emitting diode 411-2-2, ... and a 2-$n^{th}$ light-emitting diode 411-2-*n*, ... and an m-$1^{st}$ light-emitting diode 411-*m*-1, an m-$2^{nd}$ light-emitting diode 411-*m*-2, ... and an m-$n^{th}$ light-emitting diode 411-*m*-*n*, which are capable of transmitting light beams having different wavelengths.

As shown in FIG. 18, according to another aspect, in comparison to FIG. 7 and/or FIG. 14 illustrates a plurality of light-emitting diodes 411-1-1 to 411-*m*-*n* may be disposed in a matrix form in rows and columns. The plurality of light-emitting diodes 411-1-1 to 411-*m*-*n* may form a plurality of rows in a first direction D1 and may form a plurality of columns in a second direction D2.

The 1-$1^{st}$ light-emitting diode 411-1-1, the 2-$1^{st}$ light-emitting diode 411-2-1, ... and the m-$1^{st}$ light-emitting diode 411-*m*-1 may be disposed in a first column and may transmit a light beam having a first wavelength $\lambda_1$. The 1-$2^{nd}$ light-emitting diode 411-1-2, the 2-$2^{nd}$ light-emitting diode 411-2-2, ... and the m-$2^{nd}$ light-emitting diode 411-*m*-2 may be disposed in a second column and may transmit a light beam having a second wavelength $\lambda_2$. The 1-$n^{th}$ light-emitting diode 411-1-*n*, the 2-$n^{th}$ light-emitting diode 411-2-*n*, ... and the m-$n^{th}$ light-emitting diode 411-*m*-*n* may be disposed in an $n^{th}$ column and may transmit a light beam having an $n^{th}$ wavelength $\lambda_n$.

The light-emitting diode array 411 may sequentially transmit the light beam having the first wavelength $\lambda_1$, the light beam having the second wavelength $\lambda_2$, ... and the light having the $n^{th}$ wavelength $\lambda_n$ in response to an emission control signal of the controller 430. For example, the 1-1$^{st}$ light-emitting diode 411-1-1, the 2-1$^{st}$ light-emitting diode 411-2-1, . . . and the m-1$^{st}$ light-emitting diode 411-$m$-1 may sequentially transmit the light beams having the first wavelength λ1 in response to a first emission control signal of the controller 430. The 1-2$^{nd}$ light-emitting diode 411-1-2, the 2-2$^{nd}$ light-emitting diode 411-2-2, . . . and the m-2$^{nd}$ light-emitting diode 411-$m$-2 may sequentially transmit the light beams having the second wavelength $λ_2$ in response to a second emission control signal of the controller 430. In addition, the 1-n$^{th}$ light-emitting diode 411-1-$n$, the 2-n$^{th}$ light-emitting diode 411-2-$n$, . . . and the m-n$^{th}$ light-emitting diode 411-$m$-$n$ may sequentially transmit the light beams having the n$^{th}$ wavelength $λ_n$ in response to an n$^{th}$ emission control signal of the controller 430.

The light receiver 420 includes a photodiode array 421 capable of receiving light beams. The photodiode array 421 includes a first photodiode 421-1, a second photodiode 421-2, . . . and an l$^{th}$ photodiode 421-$l$.

As shown in FIG. 18, in the photodiode array 421, the first photodiode 421-1, the second photodiode 421-2, . . . and the l$^{th}$ photodiode 421-$l$ may be disposed in a line in the second direction D2.

In the photodiode array 421, all of the first photodiode 421-1, the second photodiode 421-2, . . . and the l$^{th}$ photodiode 421-$l$ may receive light beams having various wavelengths and may measure intensities of the received light beams. For example, in the photodiode array 421, all of the first photodiode 421-1, the second photodiode 421-2, . . . and the l$^{th}$ photodiode 421-$l$ may receive the light beam having the first wavelength $λ_1$, the light beam having the second wavelength $λ_2$, . . . and the light beam having the n$^{th}$ wavelength $λ_n$ and may output reception intensity signals corresponding to intensities of the received light beams.

The photodiode array 421 may receive a light beam that is transmitted from the light-emitting diode array 411 and is reflected on an object O and may transmit an electrical signal corresponding to intensity of the received light beam to the controller 430.

The controller 430 includes a processor 431 and a memory 432.

The processor 431 may generate emission control signals for sequentially turning on the plurality of light-emitting diodes 411-1-1 to 411-$m$-$n$ included in the light-emitting diode array 411. In addition, the processor 431 may sequentially store reception intensity signals received from a plurality of photodiodes 421-1, 421-2, . . . and 421-$l$ included in the photodiode array 421 in the memory 432.

The controller 430 may identify the object O based on reception intensity stored in the memory 432. In addition, the controller 430 may identify a degree of rottenness of a food or a degree of cooking of the food based on a change in the reception intensity stored in the memory 432.

The controller 430 may calculate a distance from the electronic apparatus 400 to the object O based on a time difference between a time at which the light-emitting diode array 411 transmits a light beam and a time at which the photodiode array 421 receives the light beam and based on the speed of light. The controller 430 may identify a degree of rottenness of a food or a degree of cooking of the food based on the distance from the electronic apparatus 400 to the object O and a change in the distance.

The display 490 may display information (for example, an image and/or message) about a state of the object in response to a display signal of the controller 430. For example, the display 490 may display an image and/or message indicating rottenness of a food or may display an image and/or message indicating completion of cooking of the food.

Figure 20:
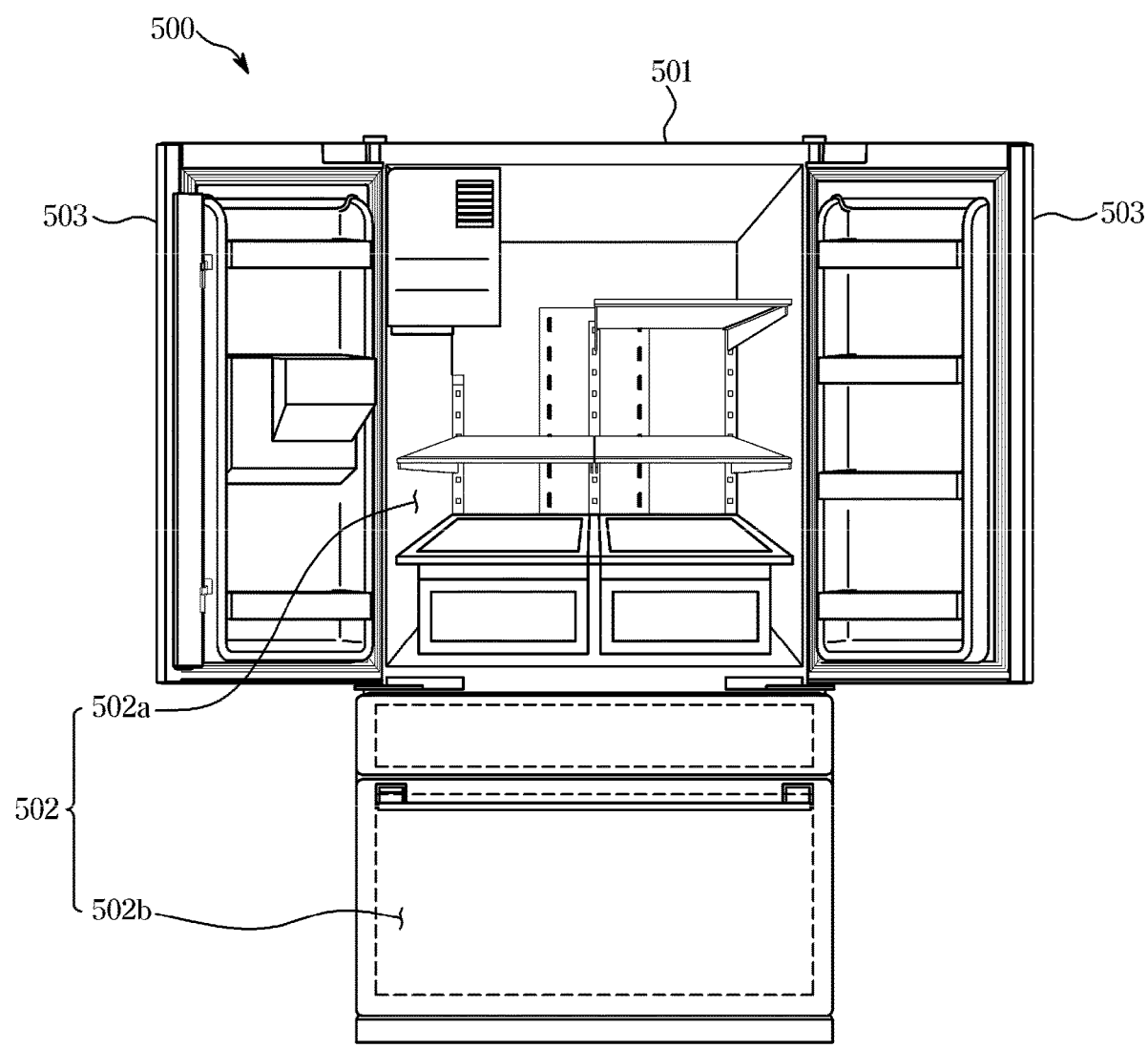
FIG. 20 is a view illustrating an exterior of a refrigerator according to one embodiment.
Figure 21:
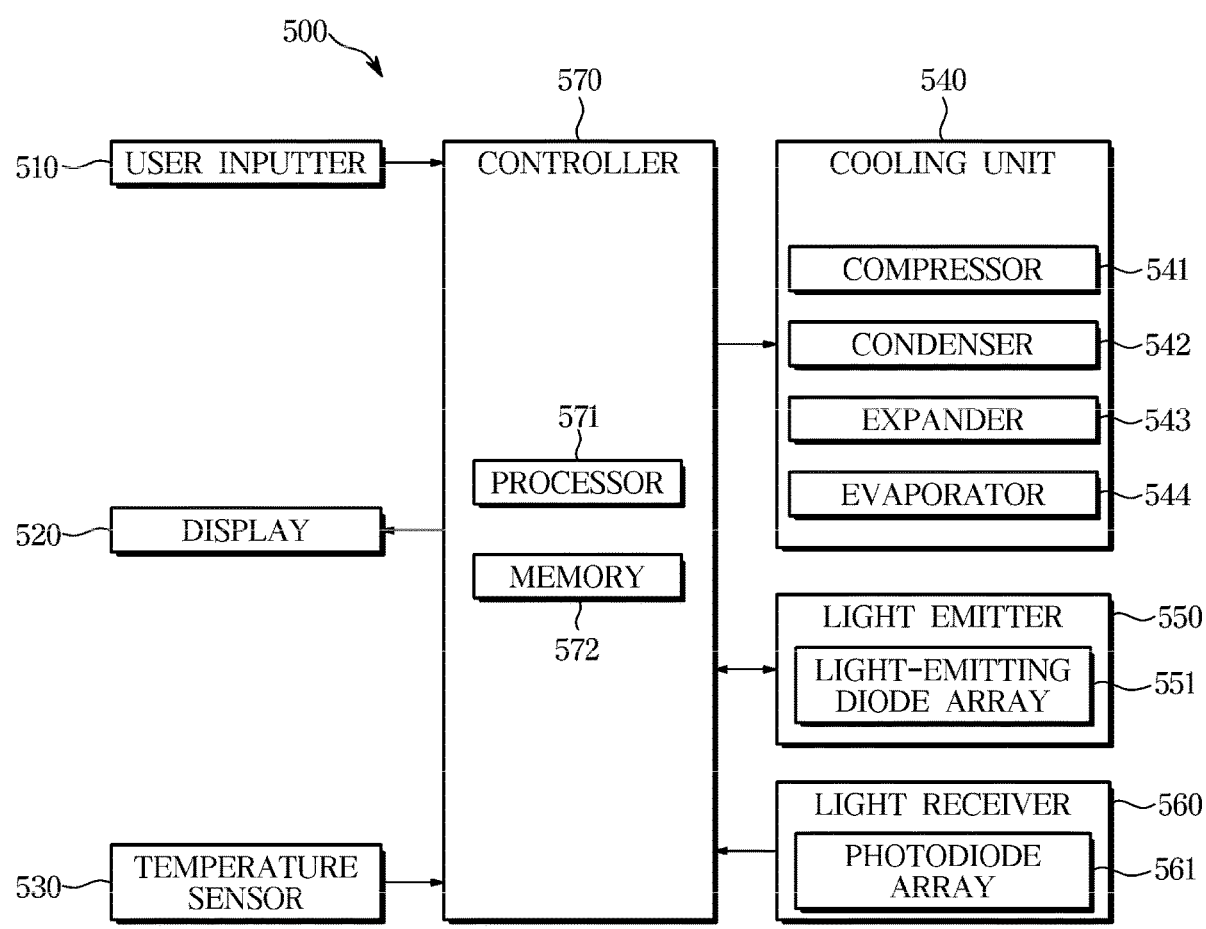
FIG. 21 is a view illustrating a configuration of the refrigerator according to one embodiment.

FIG. 20 is a view illustrating an exterior of a refrigerator according to one embodiment. FIG. 21 is a view illustrating a configuration of the refrigerator according to one embodiment.

Referring to FIGS. 20 and 21, a refrigerator 500 includes a main body 501, a storage chamber 502 provided in the main body 501 and having an open front surface, and a door 503 configured to open or close the open front surface of the storage chamber 502.

The main body 501 is formed in the form of an approximately rectangular parallelepiped box. The main body 501 may include an inner case forming the storage chamber 502 and an outer case coupled to an outer side of the inner case to form an exterior of the refrigerator 500. An insulator configured to insulate the storage chamber 502 may be provided between the inner case and the outer case.

The storage chamber 502 is provided in the main body 501. The storage chamber 502 is partitioned into an upper refrigerating chamber 502$a$ and a lower freezing chamber 502$b$ by an intermediate partition. The refrigerating chamber 502$a$ may be maintained at a temperature of about 3° C. to store a food, and the freezing chamber 502$b$ may be maintained at a temperature of about −19° C. to freeze and store a food. The front surface of the storage chamber 502 may be open so that a food may be taken in or out of the storage chamber 502.

One side of the door 503 may be rotatably attached to the main body 501 through a hinge, and the door 503 may open or close the open front surface of the storage chamber 502.

In addition, the refrigerator 500 includes a user inputter 510, a display 520, a temperature sensor 530, a cooling unit 540, a light emitter 550, a light receiver 560, and a controller 570.

The user inputter 510 and the display 520 for interacting with a user may be provided at one side of a front surface of the door 503.

The user inputter 510 may receive a user input related to operation of the refrigerator 500 from a user and may output an electrical signal (voltage or current) corresponding to the received user input to the controller 570. For example, the user inputter 510 may include a button for setting a temperature of the refrigerating chamber 502$a$, a button for setting a temperature of the freezing chamber 502$b$, and the like. The user inputter 510 may include a push switch and a membrane switch, which are operated by being pressed by a user, or a touch switch operated by being touched by a part of a user's body.

The display 520 may receive information related to the operation of the refrigerator 500 from the controller 570 and may display an image corresponding to the received information. For example, the display 520 may display a temperature of the refrigerating chamber 502$a$, a temperature of the freezing chamber 502$b$, and the like set by the user.

The temperature sensor 530 may detect a temperature inside the storage chamber 502 and may output an electrical signal (voltage or current) corresponding to the temperature inside the storage chamber 502 to the controller 570. For example, the temperature sensor 530 may include a thermistor of which an electrical resistance value is changed according to a temperature.

The cooling unit 540 includes a compressor 541 configured to compress a refrigerant in a gas state, a condenser 542 configured to convert the compressed refrigerant from the gas state to a liquid state, an expander 543 configured to reduce pressure of the refrigerant in the liquid state, and an evaporator 544 configured to convert the pressure-reduced refrigerant from the liquid state to the gas state.

The refrigerant may be circulated through the compressor 541, the condenser 542, the expander 543, and the evaporator 544, may absorb thermal energy from the storage chamber 502, and may discharge the absorbed thermal energy to the outside of the refrigerator 500. Specifically, the refrigerant may absorb thermal energy while being evaporated in the evaporator 544 provided in the storage chamber 502. In addition, the refrigerant may discharge the thermal energy while being condensed in the condenser 542 provided outside the storage chamber 502.

As described above, the refrigerant absorbs thermal energy in the evaporator 544, and thus, air in the storage chamber 502 is cooled.

The light emitter 550 includes a light-emitting diode array 551 capable of transmitting a plurality of light beams having different wavelengths.

The light-emitting diode array 551 may include, for example, a first light-emitting diode configured to transmit a light beam having a first wavelength $\lambda_1$, a second light-emitting diode configured to transmit a light beam having a second wavelength $\lambda_2$, ... and an $n^{th}$ light-emitting diode configured to transmit a light beam having an $n^{th}$ wavelength $\lambda_n$. The first light-emitting diode, the second light-emitting diode, ... and the $n^{th}$ light-emitting diode may be disposed in a line or a matrix form in rows and columns.

The light-emitting diode array 551 may sequentially transmit the light beam having the first wavelength $\lambda_1$, the light beam having the second wavelength $\lambda_2$, ... and the light beam having the $n^{th}$ wavelength $\lambda_n$ in response to an emission control signal of the controller 570.

The light receiver 560 includes a photodiode array 561 capable of receiving light beams having various wavelengths.

The photodiode array 561 may include, for example, a first photodiode, a second photodiode, ... and an $n^{th}$ photodiode, which are capable of receiving the light beams having the first wavelength $\lambda_1$, the second wavelength $\lambda_2$, ... and the $n^{th}$ wavelength $\lambda_n$. The first photodiode, the second photodiode, ... and the $n^{th}$ photodiode may be disposed in a line or a matrix form in rows and columns.

The photodiode array 561 may receive the light beam having the first wavelength $\lambda_1$, the second wavelength $\lambda_2$, ... or the $n^{th}$ wavelength $\lambda_n$ and may output a reception intensity signal corresponding to intensity of the received light beam to the controller 570.

The controller 570 may be electrically connected to the user inputter 510, the display 520, the temperature sensor 530, the cooling unit 540, the light emitter 550, and the light receiver 560.

The controller 570 includes a processor 571 and a memory 572.

The processor 571 may process a user input received by the user inputter 510 and temperature information measured by the temperature sensor 530 and may generate a cooling control signal for controlling operation of the cooling unit 540. The processor 571 may include an operational circuit, a memory circuit, and a control circuit. The processor 571 may include one chip or may include a plurality of chips.

The memory 572 may store and/or retain a program and data for controlling operation of the refrigerator 500. The memory 572 may include volatile memories such as an S-RAM and a D-RAM and nonvolatile memories such as a ROM and an EPROM. The memory 572 may include one memory element or may include a plurality of memory elements.

As described above, the controller 570 may control the operation of the cooling unit 540 based on a temperature of the storage chamber 502.

In addition, the controller 570 may control the light emitter 550 and the light receiver 560 to identify a degree of rottenness of a food stored in the storage chamber 502.

The controller 570 may identify an object O based on a user input.

The controller 570 may control the light-emitting diode array 551 to sequentially transmit the light beam having the first wavelength $\lambda_1$, the light beam having the second wavelength $\lambda_2$, ... and the light beam having the $n^{th}$ wavelength $\lambda_n$. In addition, the controller 570 may sequentially store reception intensities (reflection intensities) received by the photodiode array 561 in the memory 572.

The controller 570 may identify a degree of rottenness of a food based on reflection intensity (or reflectance) of the light beam having the first wavelength $\lambda_1$, reflection intensity (or reflectance) of the light beam having the second wavelength $\lambda_2$, ... and reflection intensity (reflectance) of the light beam having the $n^{th}$ wavelength $\lambda_n$.

For example, the controller 570 may calculate a rottenness value of a food by respectively inputting measured reflection intensity of the light beam having the first wavelength $\lambda_1$, measured reflection intensity of the light beam having the second wavelength $\lambda_2$, ... and measured reflection intensity of the light beam having the $n^{th}$ wavelength $\lambda_n$ in $x_1, x_2, \ldots$ and $x_n$ of Expression 1. The controller 570 may identify a degree of rottenness of a food stored in the storage chamber 502 based on a rottenness value of the food.

The controller 570 may identify a degree of rottenness of a food based on a change in reflection intensity (or reflectance) of the light beam having the first wavelength $\lambda_1$, a change in reflection intensity (or reflectance) of the light beam having the second wavelength $\lambda_2$, ... and a change in reflection intensity (reflectance) of the light beam having the $n^{th}$ wavelength $\lambda_n$.

When it is identified that a food has been rotten, the controller 570 may display an image and/or message indicating the rottenness of the food on the display 520.

Figure 22:
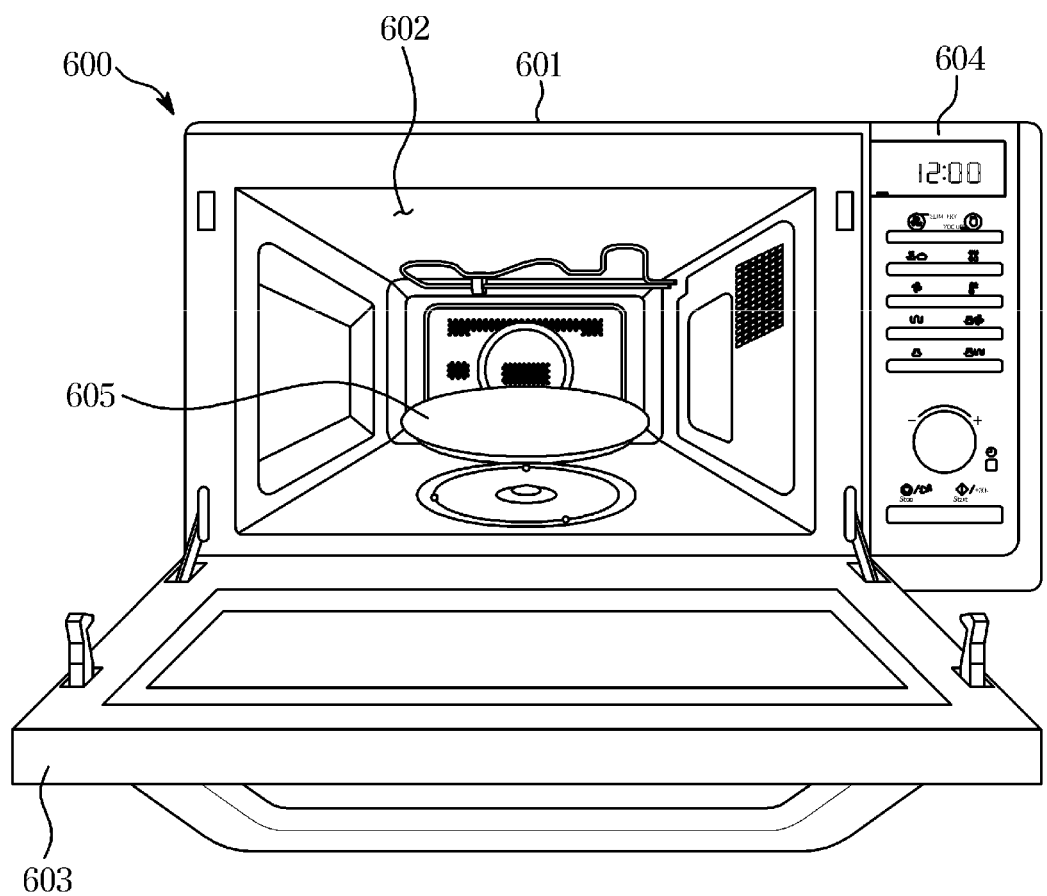
FIG. 22 is a view illustrating an exterior of a cooking apparatus according to one embodiment.
Figure 23:
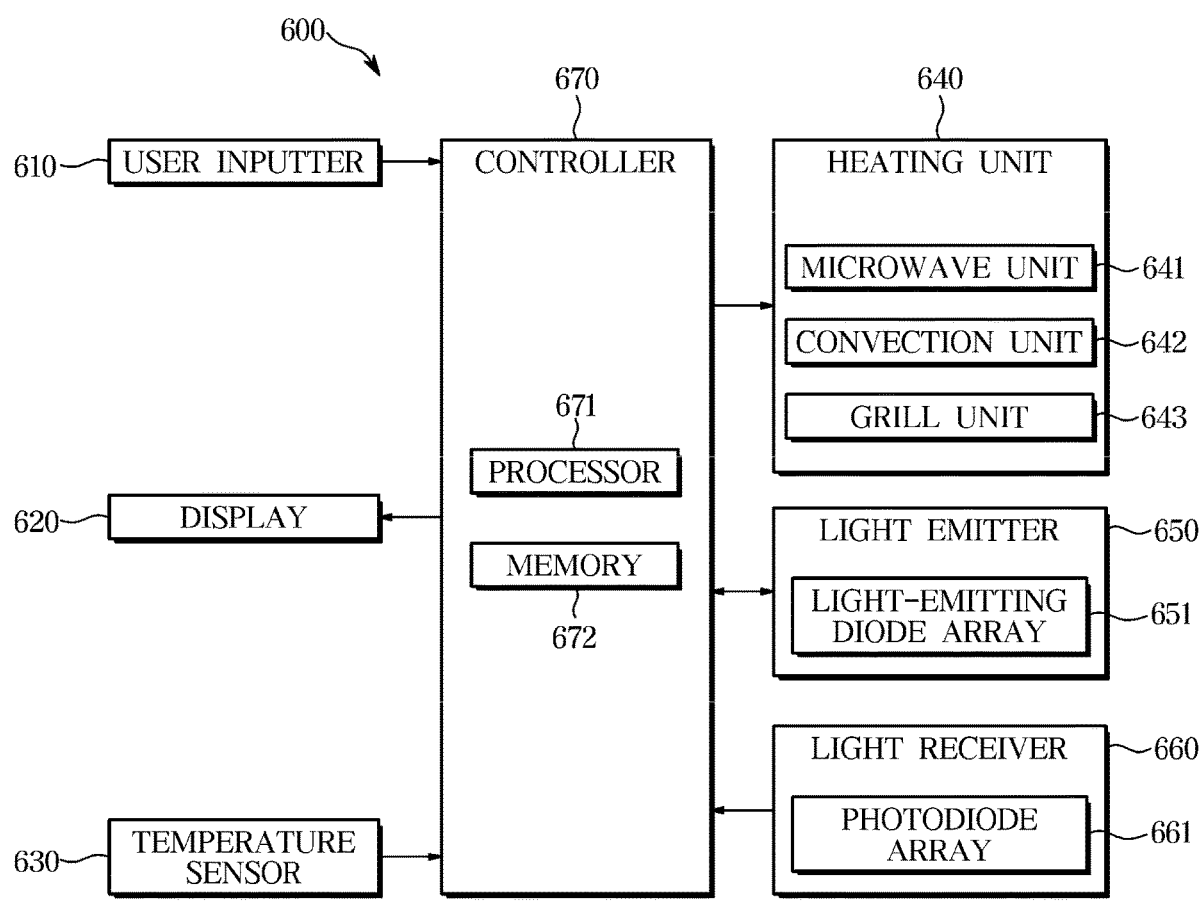
FIG. 23 is a view illustrating a configuration of the cooking apparatus according to one embodiment.

FIG. 22 is a view illustrating an exterior of a cooking apparatus according to one embodiment. FIG. 23 is a view illustrating a configuration of the cooking apparatus according to one embodiment.

Referring to FIGS. 22 and 23, a cooking apparatus 600 includes a main body 601, a cooking chamber 602 provided in the main body 601 and having an open front surface, and a door 603 configured to open or close the open front surface of the cooking chamber 602.

The main body 601 is formed in the form of an approximately rectangular parallelepiped box. A control panel 604 configured to receive a user input and display operation information of the cooking apparatus 600 may be provided at one side of a front surface of the main body 601.

The cooking chamber 602 may be provided in the main body 601 and may also be formed in the form of an approximately rectangular parallelepiped box. The cooking chamber 602 is provided with a turntable 605 on which an object to be cooked may be placed. In addition, the front surface of the cooking chamber 602 may be open so that the object to be cooked may be taken in or out of the cooking chamber 602.

One side of the door 603 may be rotatably attached to the main body 601 through a hinge, and the door 603 may open or close the open front surface of the cooking chamber 602.

The cooking apparatus 600 also includes a user inputter 610, a display 620, a temperature sensor 630, a heating unit 640, a light emitter 650, a light receiver 660, and a controller 670.

The user inputter 610 and the display 620 for interacting with a user may be provided in the control panel 604.

The user inputter 610 may receive a user input related to operation of the cooking apparatus 600 from a user and may output an electrical signal (voltage or current) corresponding to the received user input to the controller 670. For example, the user inputter 610 may include a plurality of buttons for receiving a cooking course and a dial for receiving a cooking time or weight of an object to be cooked.

The display 620 may receive information related to operation of the cooking apparatus 600 from the controller 670 and may display an image corresponding to the received information. For example, the display 620 may display a cooking course selected by a user or may display a cooking time left until cooking is completed.

The temperature sensor 630 may detect a temperature inside the cooking chamber 602 and may output an electrical signal (voltage or current) corresponding to the temperature inside the cooking chamber 602 to the controller 670.

The heating unit 640 includes a microwave unit 641, a convection unit 642, and a grill unit 643.

The microwave unit 641 may include a magnetron configured to generate a microwave of about 2.45 GHz and an antenna configured to irradiate a microwave into the cooking chamber 602. The microwave unit 641 may irradiate the microwave of about 2.45 GHz into the cooking chamber 602 to heat an object to be cooked which is disposed in the cooking chamber 602.

The convection unit 642 may include a heater configured to heat air and a fan configured to blow the heated air into the cooking chamber 602. The convection unit 642 may blow the heated air into the cooking chamber 602 to heat the object to be cooked disposed in the cooking chamber 602.

The grill unit 643 may include a heater capable of emitting radiant heat. The grill unit 643 may heat the object to be cooked disposed in the cooking chamber 602 using the radiant heat emitted from the heater.

The light emitter 650 includes a light-emitting diode array 651 capable of transmitting a plurality of light beams having different wavelengths.

The light-emitting diode array 651 may include, for example, a first light-emitting diode configured to transmit a light beam having a first wavelength $\lambda_1$, a second light-emitting diode configured to transmit a light beam having a second wavelength $\lambda_2$, ... and an $n^{th}$ light-emitting diode configured to transmit a light beam having an $n^{th}$ wavelength $\lambda_n$. The first light-emitting diode, the second light-emitting diode, ... and the $n^{th}$ light-emitting diode may be disposed in a line or a matrix form in rows and columns.

The light-emitting diode array 651 may sequentially transmit the light beam having the first wavelength $\lambda_1$, the light beam having the second wavelength $\lambda_2$, ... and the light beam having the $n^{th}$ wavelength $\lambda_n$ in response to an emission control signal of the controller 670.

The light receiver 660 includes a photodiode array 661 capable of receiving light beams having various wavelengths.

The photodiode array 661 may include, for example, a first photodiode, a second photodiode, ... and an $n^{th}$ photodiode, which are capable of receiving the light beams having the first wavelength $\lambda_1$, the second wavelength $\lambda_2$, ... and the $n^{th}$ wavelength $\lambda_n$. The first photodiode, the second photodiode, ... and the $n^{th}$ photodiode may be disposed in a line or a matrix form in rows and columns.

The photodiode array 661 may receive the light beam having the first wavelength $\lambda_1$, the second wavelength $\lambda_2$, ... or the $n^{th}$ wavelength $\lambda_n$ and may output a reception intensity signal corresponding to intensity of the received light beam to the controller 670.

The controller 670 may be electrically connected to the user inputter 610, the display 620, the temperature sensor 630, the heating unit 640, the light emitter 650, and the light receiver 660.

The controller 670 includes a processor 671 and a memory 672.

The memory 672 may store and/or retain a program and data for controlling the cooking apparatus 600.

The processor 671 may process a user input received by the user inputter 610 and temperature information measured by the temperature sensor 630 and may generate a heating control signal for controlling operation of the heating unit 640. The processor 671 may include an operational circuit, a memory circuit, and a control circuit. The processor 671 may include one chip or may include a plurality of chips.

The memory 672 may store and/or retain a program and data for controlling operation of the cooking apparatus 600. The memory 672 may include volatile memories such as an S-RAM and a D-RAM and nonvolatile memories such as a ROM and an EPROM. The memory 672 may include one memory element or may include a plurality of memory elements.

As described above, the controller 670 may control operation of the heating unit 640 based on a temperature of the cooking chamber 602.

In addition, the controller 670 may control the light emitter 650 and the light receiver 660 to identify a degree of cooking of a food disposed in the cooking chamber 602.

The controller 670 may identify an object O based on a user input.

The controller 670 may control the light-emitting diode array 651 to sequentially transmit the light beam having the first wavelength $\lambda_1$, the light beam having the second wavelength $\lambda_2$, ... and the light beam having the $n^{th}$ wavelength $\lambda_n$. In addition, the controller 670 may sequentially store reception intensities (reflection intensities) received by the photodiode array 661 in the memory 672.

The controller 670 may identify a degree of cooking of a food based on reflection intensity (or reflectance) of the light beam having the first wavelength $\lambda_1$, reflection intensity (or reflectance) of the light beam having the second wavelength $\lambda_2$, ... and reflection intensity (reflectance) of the light beam having the $n^{th}$ wavelength $\lambda_n$. For example, the controller 670 may calculate a rottenness value of a food by respectively inputting measured reflection intensity of the light beam having the first wavelength $\lambda_1$, measured reflection intensity of the light beam having the second wavelength $\lambda_2$, ... and measured reflection intensity of the light beam having the $n^{th}$ wavelength $\lambda_n$ in $x_1$, $x_2$, ... and $x_n$ of Expression 1. The controller 670 may identify a degree of cooking of a food stored in the cooking chamber 602 based on a rottenness value of the food.

The controller 670 may identify a degree of rottenness of a food based on a change in reflection intensity (or reflectance) of the light beam having the first wavelength $\lambda_1$, a change in reflection intensity (or reflectance) of the light beam having the second wavelength $\lambda_2$, ... and a change in reflection intensity (reflectance) of the light beam having the $n^{th}$ wavelength $\lambda_n$.

The controller 670 may measure distances from the light-emitting diode array 651 and the photodiode array 661 to a food. The controller 670 may calculate a distance to the object O based on a time difference between a time at which the light-emitting diode array 651 transmits a light beam and a time at which the photodiode array 661 receives the light beam and based on the speed of light.

The controller 670 may identify cooking information of a food based on a change in distance to the object O according to a time. In general, it is known that a volume of a food is reduced due to moisture being evaporated as the food is cooked. When an increased value of the distance to the object O is greater than or equal to a reference distance and a change rate of the distance to the object O is less than or equal to a reference change rate, the controller 670 may determine that the cooking of the food has been completed.

When it is identified that the cooking of the food has been completed, the controller 670 may stop the operation of the heating unit 640 and may display an image and/or message indicating the completion of cooking of the food on the display 620.

As is apparent from the above description, an electronic apparatus may include a light-emitting diode array capable of transmitting light beams having different wavelengths, a photodiode array capable of receiving light beams, a display, and a processor configured to control the light-emitting diode array to transmit the light beams having the different wavelengths toward an object, identify a state of the object based on reception intensities of the light beams having the different wavelengths received by the photodiode array, and display information about the state of the object on the display.

By using a plurality of light-emitting diodes capable of transmitting a plurality of light beams having different wavelengths, the electronic apparatus may more accurately identify the state of the object.

The processor may identify the state of the object based on whether the reception intensities of the received light beams having the different wavelengths are less than or equal to a plurality of reference intensities predefined with respect to the light beams having the different wavelengths.

In addition, the electronic apparatus may further include a storage chamber configured to store the object and a cooling unit configured to cool the storage chamber. The processor may display an image or a message indicating rottenness of the object on the display in response to the reception intensities of the received light beams having the different wavelengths being less than or equal to the plurality of predefined reference intensities.

Furthermore, the electronic apparatus may further include a cooking chamber in which the object is placed and a heating unit configured to heat the cooking chamber. The processor may display an image or a message indicating completion of cooking of the object on the display in response to the reception intensities of the received light beams having the different wavelengths being less than or equal to the plurality of predefined reference intensities.

Therefore, the electronic apparatus may use reflectances in which the plurality of light beams having the different wavelengths are reflected on the object so that the electronic apparatus may more accurately identify whether the object is rotten and/or whether the cooking of the object is completed.

The processor may identify the state of the object based on whether change values of the reception intensities of the received light beams having the different wavelengths are less than or equal to a plurality of reference change values predefined with respect to the light beams having the different wavelengths.

In addition, the electronic apparatus may further include a storage chamber configured to store the object and a cooling unit configured to cool the storage chamber. The processor may display an image or a message indicating rottenness of the object on the display in response to the change values of the reception intensities of the received light beams having the different wavelengths being less than or equal to the plurality of predefined reference change values.

Furthermore, the electronic apparatus may further include a cooking chamber in which the object is placed and a heating unit configured to heat the cooking chamber. The processor may display an image or a message completion of cooking of the object on the display in response to the change values of the reception intensities of the received light beams having the different wavelengths being less than or equal to the plurality of predefined reference change values.

Therefore, the electronic apparatus may use change rates of reflectances in which the plurality of light beams having the different wavelengths are reflected on the object so that the electronic apparatus may more accurately identify whether the object is rotten and/or whether the cooking of the object is completed.

The light-emitting diode array may include a plurality of light-emitting diodes capable of transmitting light beams having different wavelengths, and the photodiode array may include one photodiode.

In addition, the processor may sequentially turn on the plurality of light-emitting diodes and may process intensity of the light beam received by the photodiode in response to one of the plurality of light-emitting diodes being turned on.

As described above, by using the light-emitting diodes and the photodiode, the electronic apparatus may identify the state of the object at a low cost.

The light-emitting diode array may include a plurality of light-emitting diodes disposed in a line in a first direction and configured to transmit light beams having different wavelengths, and the photodiode array may include a plurality of photodiodes disposed in a line in a second direction orthogonal to the first direction.

In addition, the processor may sequentially turn on the plurality of light-emitting diodes and may process intensity of the light beam received by each of the plurality of photodiodes in response to one of the plurality of light-emitting diodes being turned on.

As described above, by using the linearly disposed light-emitting diodes and the linearly disposed photodiodes, the electronic apparatus may calculate reflectances of the light beams having the different wavelengths on an entire surface of the object and may also identify a state of a specific portion of the object.

The light-emitting diode array may include a plurality of light-emitting diodes capable of transmitting light beams having different wavelengths, and the photodiode array may include a plurality of photodiodes disposed in rows and columns.

In addition, the processor may sequentially turn on the plurality of light-emitting diodes and may process intensity of the light beam received by each of the plurality of photodiodes in response to one of the plurality of light-emitting diodes being turned on.

As described above, by using the linearly disposed light-emitting diodes and the two-dimensionally disposed photodiodes, the electronic apparatus may calculate reflectances of the light beams having the different wavelengths on an entire surface of the object and may also identify a state of a specific portion of the object.

The light-emitting diode array may include a plurality of light-emitting diodes disposed in columns and rows, the light-emitting diodes disposed in different columns may transmit light beams having different wavelengths, and the photodiode array may include a plurality of photodiodes disposed in a line.

As described above, by using the two-dimensionally disposed light-emitting diodes and the linearly disposed photodiodes, the electronic apparatus may calculate reflectances of the light beams having the different wavelengths on an entire surface of the object and may also identify a state of a specific portion of the object.

According to an aspect of the present disclosure, it is possible to provide an electronic apparatus using a plurality of light beams having different wavelengths.

According to an aspect of the present disclosure, it is possible to provide an electronic apparatus capable of identifying a state of an object using a plurality of light beams having different wavelengths.

According to an aspect of the present disclosure, it is possible to provide an electronic apparatus capable of identifying cooking information of a food using a plurality of light beams having different wavelengths.

According to an aspect of the present disclosure, it is possible to provide an electronic apparatus capable of identifying whether a food is rotten using a plurality of light beams having different wavelengths.

Exemplary embodiments of the present disclosure have been described above. In the exemplary embodiments described above, some components may be implemented as a "module". Here, the term 'module' means, but is not limited to, a software and/or hardware component, such as a Field Programmable Gate Array (FPGA) or Application Specific Integrated Circuit (ASIC), which performs certain tasks. A module may advantageously be configured to reside on the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

With that being said, and in addition to the above described exemplary embodiments, embodiments can thus be implemented through computer readable code/instructions in/on a medium, e.g., a computer readable medium, to control at least one processing element to implement any above described exemplary embodiment. The medium can correspond to any medium/media permitting the storing and/or transmission of the computer readable code.

The computer-readable code can be recorded on a medium or transmitted through the Internet. The medium may include Read Only Memory (ROM), Random Access Memory (RAM), Compact Disk-Read Only Memories (CD-ROMs), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the attached claims.

What is claimed is:

1. An electronic apparatus comprising:
   a light-emitting diode array configured to transmit light beams having different wavelengths;
   a photodiode;
   a display; and
   a processor configured to:
      control the light-emitting diode array to transmit the light beams having the different wavelengths toward an object,
      identify a state of the object based on intensities received by the photodiode according to light beams having the different wavelengths that are reflected on the object, and
      control the display to display information about the state of the object,
   wherein the processor identifies the state of the object based on whether the intensities received by the photodiode according to the reflected light beams having the different wavelengths are less than or equal to a plurality of reference intensities predefined with respect to the light beams having the different wavelengths.

2. The electronic apparatus of claim 1, further comprising a storage chamber configured to store the object and a cooling unit configured to cool the storage chamber,
   wherein the processor controls the display to display the state of the object using an image or a message indicating rottenness of the object in response to the intensities received by the photodiode according to the reflected light beams having the different wavelengths being less than or equal to the plurality of predefined reference intensities.

3. The electronic apparatus of claim 1, further comprising a cooking chamber in which the object is placed and a heating unit configured to heat the cooking chamber,
   wherein the processor controls the display to display the state of the object using an image or a message indicating completion of cooking of the object in response to the intensities received by the photodiode according to the reflected light beams having the different wavelengths being less than or equal to the plurality of predefined reference intensities.

4. The electronic apparatus of claim 1, wherein the processor identifies the state of the object based on whether change values of the intensities received by the photodiode according to the reflected light beams having the different wavelengths are less than or equal to a plurality of reference change values predefined with respect to the light beams having the different wavelengths.

5. The electronic apparatus of claim 4, further comprising a storage chamber configured to store the object and a cooling unit configured to cool the storage chamber, wherein the processor controls the display to display the state of the object using an image or a message indicating rottenness of the object in response to the change values of the intensities received by the photodiode according to the reflected light beams having the different wavelengths being less than or equal to the plurality of predefined reference change values.

6. The electronic apparatus of claim 4, further comprising a cooking chamber in which the object is placed and a heating unit configured to heat the cooking chamber,
wherein the processor controls the display to display the state of the object using an image or a message indicating completion of cooking of the object on the display in response to the change values of the intensities received by the photodiode according to the reflected light beams having the different wavelengths being less than or equal to the plurality of predefined reference change values.

7. The electronic apparatus of claim 1, wherein the light-emitting diode array includes a plurality of light-emitting diodes configured to transmit the light beams having the different wavelengths, and
the photodiode includes one photodiode.

8. The electronic apparatus of claim 7, wherein the processor sequentially turns on the plurality of light-emitting diodes and processes an intensity of the light beam received by the one photodiode in response to one of the plurality of light-emitting diodes being turned on.

9. The electronic apparatus of claim 1, wherein the light-emitting diode array includes a plurality of light-emitting diodes disposed in a line in a first direction and configured to transmit the light beams having the different wavelengths, and
the photodiode includes a plurality of photodiodes disposed in a line in a second direction orthogonal to the first direction.

10. The electronic apparatus of claim 9, wherein the processor sequentially turns on the plurality of light-emitting diodes and processes an intensity of the light beam received by each of the plurality of photodiodes in response to one of the plurality of light-emitting diodes being turned on.

11. The electronic apparatus of claim 1, wherein the light-emitting diode array includes a plurality of light-emitting diodes configured to transmit the light beams having the different wavelengths, and
the photodiode includes a plurality of photodiodes disposed in columns and rows.

12. The electronic apparatus of claim 11, wherein the processor sequentially turns on the plurality of light-emitting diodes and processes an intensity of the light beam received by each of the plurality of photodiodes in response to one of the plurality of light-emitting diodes being turned on.

13. The electronic apparatus of claim 1, wherein the light-emitting diode array includes a plurality of light-emitting diodes disposed in rows and columns,
the light-emitting diodes disposed in different columns transmit the light beams having the different wavelengths, and
the photodiode includes a plurality of photodiodes disposed in a line.

14. A controlling method of an electronic apparatus, comprising:
transmitting, by a light-emitting diode array, light beams having different wavelengths toward an object;
receiving, by a photodiode, the light beams having the different wavelengths reflected on the object;
identifying a state of the object based on intensities received by the photodiode according to the reflected light beams having the different wavelengths; and
displaying information about the state of the object on a display,
wherein the identifying of the state of the object includes identifying the state of the object based on whether the intensities received by the photodiode according to the reflected light beams having the different wavelengths are less than or equal to a plurality of reference intensities predefined with respect to the light beams having the different wavelengths.

15. The controlling method of claim 14, wherein the displaying of the information about the state of the object on the display includes displaying an image or a message indicating rottenness of the object or completion of cooking of the object on the display in response to the intensities received by the photodiode according to the reflected light beams having the different wavelengths being less than or equal to the plurality of predefined reference intensities.

16. The controlling method of claim 14, wherein the identifying of the state of the object includes identifying the state of the object based on whether change values of the intensities received by the photodiode according to the reflected light beams having the different wavelengths are less than or equal to a plurality of reference change values predefined with respect to the light beams having the different wavelengths.

17. The controlling method of claim 16, wherein the displaying of the information about the state of the object on the display includes displaying an image or a message indicating rottenness of the object or completion of cooking of the object on the display in response to the change values of the intensities received by the photodiode according to the reflected light beams having the different wavelengths being less than or equal to the plurality of predefined reference change values.

18. An electronic apparatus comprising:
a chamber configured to accommodate a food;
a plurality of light-emitting diodes configured to transmit light beams having different wavelengths;
a plurality of photodiodes;
a display; and
a processor configured to:
control the plurality of light-emitting diodes to sequentially transmit the light beams having the different wavelengths toward the food which is accommodated in the chamber, and
control the display to display a state of the food based on intensities received by the plurality of photodiodes according to light beams having the different wavelengths that are reflected on the object.

* * * * *